United States Patent
Burns et al.

(10) Patent No.: US 7,411,002 B2
(45) Date of Patent: Aug. 12, 2008

(54) POLYCATIONIC SULFONAMIDES AND USE THEREOF

(75) Inventors: Mark R. Burns, Kenmore, WA (US); Sunil A. David, Lawrence, KS (US); Scott A. Jenkins, Tucson, AZ (US)

(73) Assignees: The University of Kansas, Lawrence, KS (US); Mediquest Therapeutics, Inc., Bothell, WA (US)

( * ) Notice: Subject to any disclaimer, the term of this patent is extended or adjusted under 35 U.S.C. 154(b) by 58 days.

(21) Appl. No.: 11/447,865

(22) Filed: Jun. 7, 2006

(65) Prior Publication Data

US 2007/0287750 A1  Dec. 13, 2007

(51) Int. Cl.
  *A61K 31/18* (2006.01)
  *C07C 311/05* (2006.01)
(52) U.S. Cl. .................... 514/601; 564/82; 564/98
(58) Field of Classification Search ......... 514/601; 564/82, 98
  See application file for complete search history.

(56) References Cited

U.S. PATENT DOCUMENTS 6,646,149 B1 * 11/2003 Vermeulin et al. ............ 560/25
6,919,483 B2 * 7/2005 Burns et al. .................. 564/453

FOREIGN PATENT DOCUMENTS

WO  WO-99/03823 A2  1/1999

OTHER PUBLICATIONS

Chem. Abst. 134:157282: Effect of the polyamine oxidase inactivator MDL 72527 on N1-(n-octanesulfonyl)spermine toxiticiy. (2000).*
Seiler, N. et al. "Inhibition of polyamine oxidase enhances the cytotoxicity of polyamine oxidase substrates. A model study with $N^1$-(n-octanesulfonyl)spermine and human colon cancer cells," *The International Journal of Biochemistry & Cell Biology*, vol. 32, p. 703-716, (2000).
Cromer, J.R., et al. "Functionalized dendrimers as endotoxin sponges," *Bioorganic & Medicinal Chemistry Letters*, vol. 15, p. 1295-1298, (2005).
Parratt, J.R. "Nitric oxide in sepsis and endotoxaemia," *Journal of Antimicrobial Chemotherapy*, vol. 41, p. 31-39, (1998).
Elner, S.G., et al. "TLR4 Mediates Human Retinal Pigment Epithelial Endotoxin Binding and Cytokine Expression," *Trans Am Ophthalmol Soc*, vol. 103, p. 126-137, (2005).
Basu S., et al. "Toll-like receptors: function and roles in lung disease," *Am J Physiol Lung Cell Mol Physiol*, vol. 286, p. 887-892, (2004).
Tzouros, M., et al. "New linear polyamine derivatives in spider venoms," *Toxicon*, vol. 46, p. 350-354, (2005).

\* cited by examiner

*Primary Examiner*—Peter G O'Sullivan
(74) *Attorney, Agent, or Firm*—Connolly Bove Lodge & Hutz, LLP

(57) ABSTRACT

Certain lipophilic polycationic sulfonamides are provided and are useful for treating various diseases or conditions and particularly sepsis.

18 Claims, 11 Drawing Sheets

Figure 1: Schematic of lipopolysaccharide target.
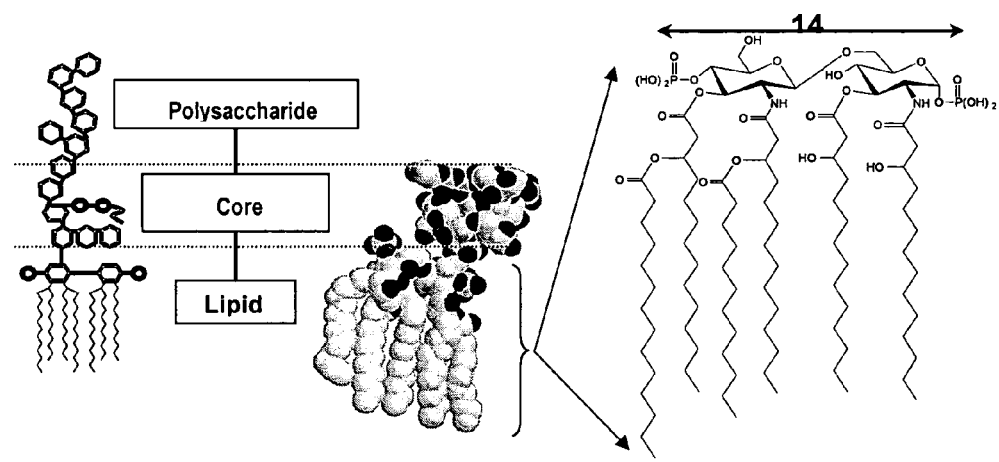

Figure 2a: Ability of polycationic sulfonamides to bind LPS.
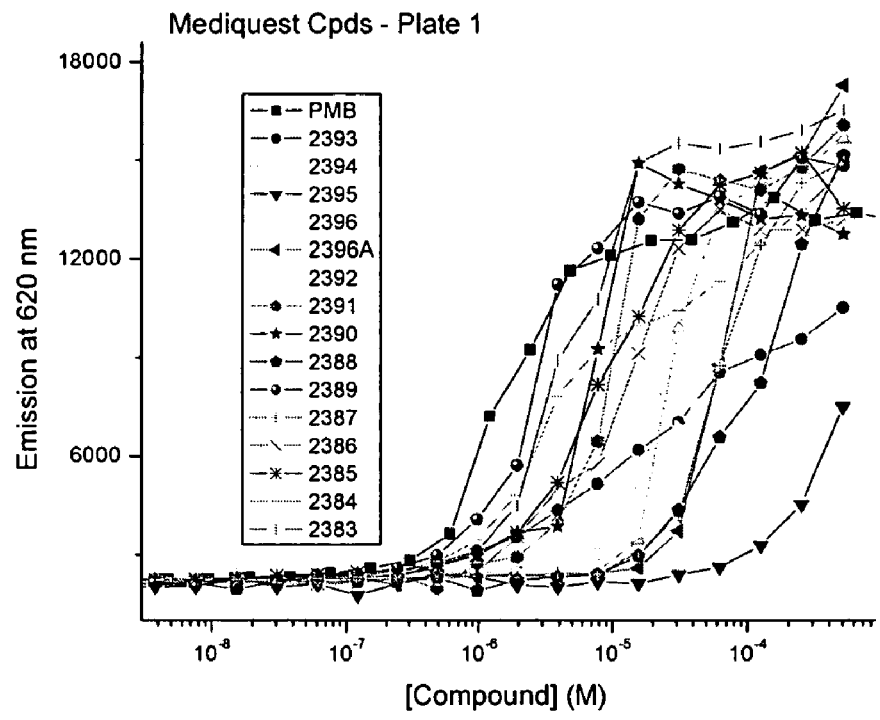
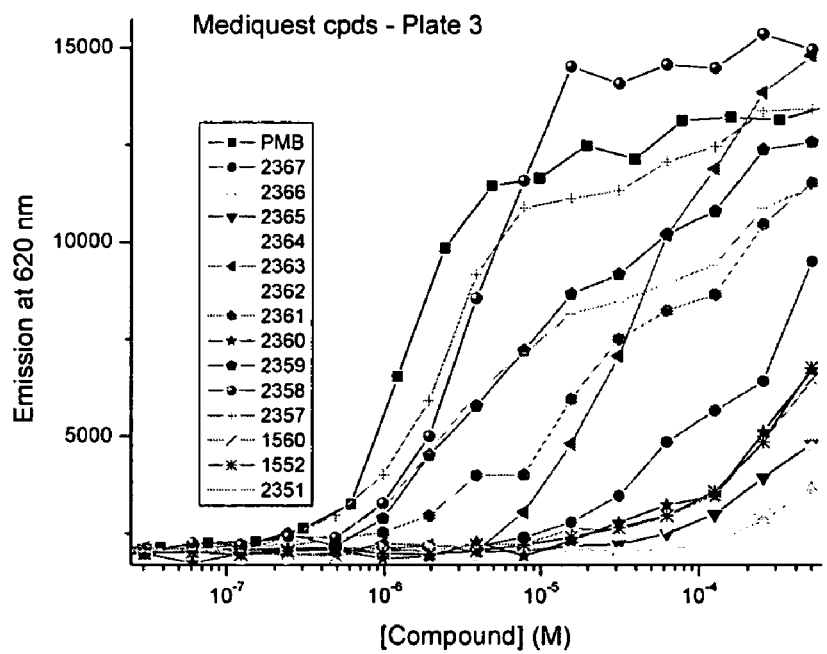

Figure 2b: Ability of polycationic sulfonamides to bind LPS.
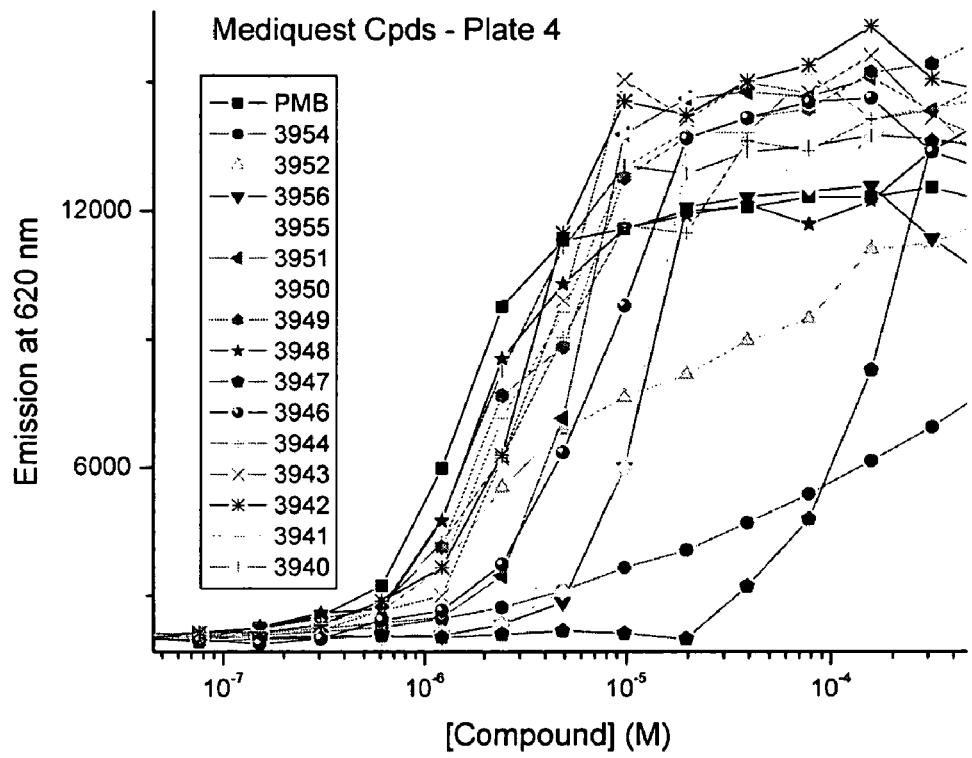
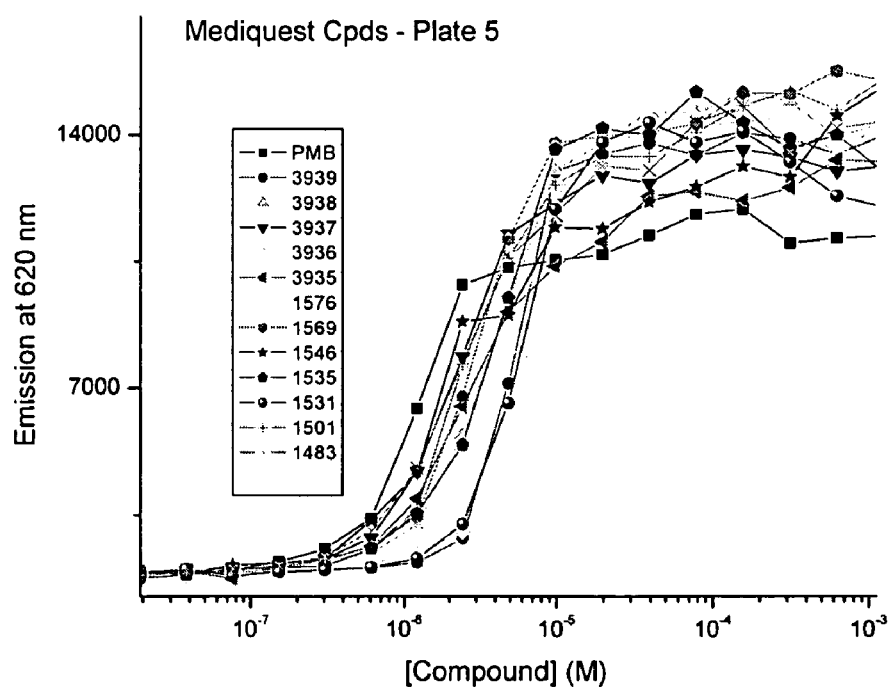

Figure 3a: Ability of polycationic sulfonamides to inhibit cytokine production.
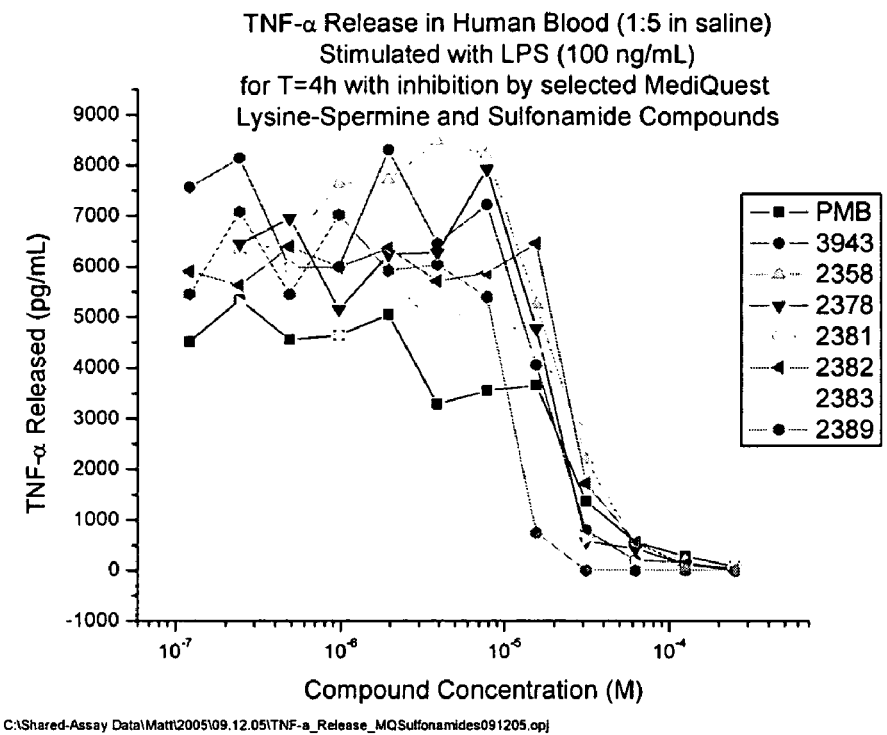
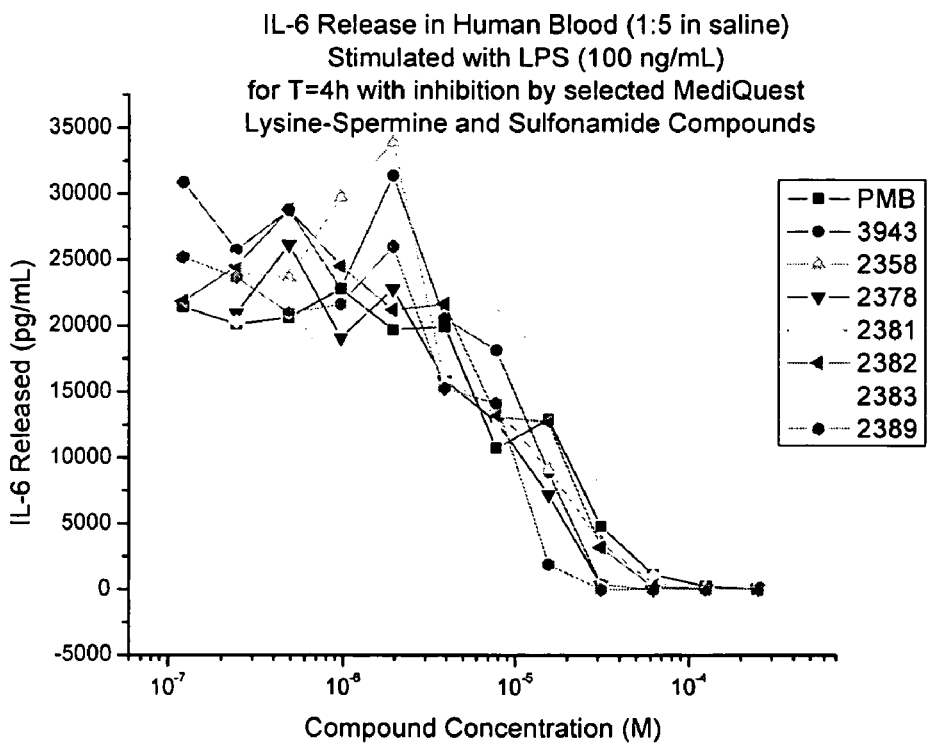

Figure 3b: Ability of polycationic sulfonamides to inhibit cytokine production.
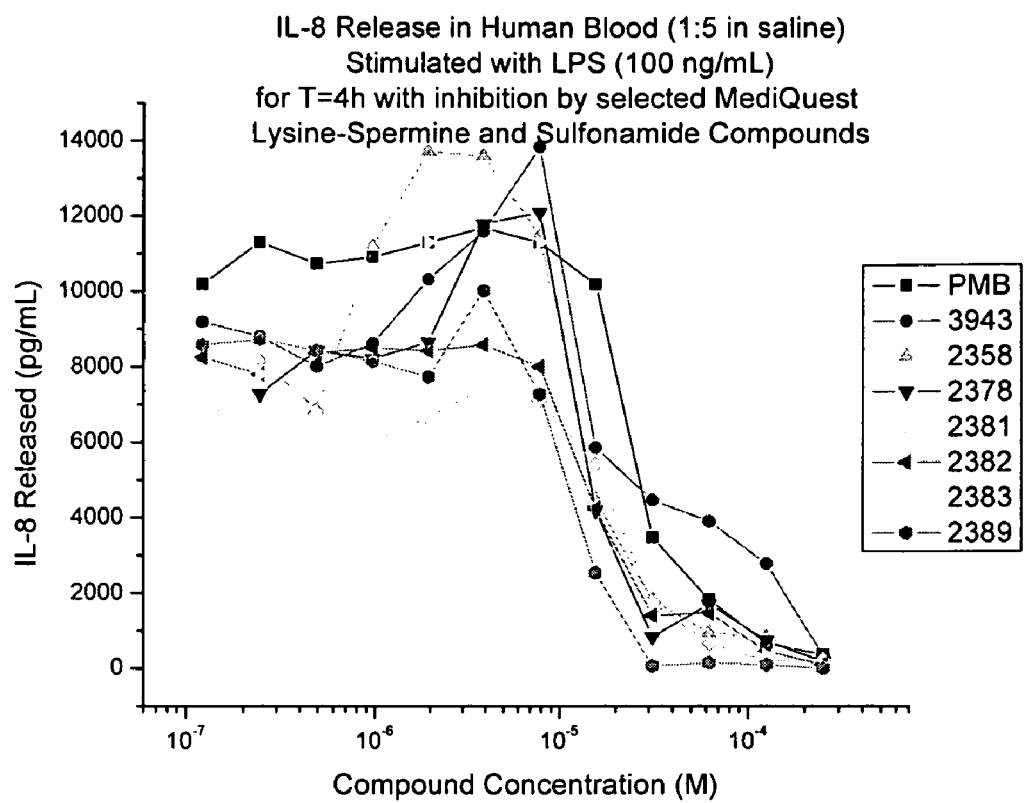

Figure 4: Synthesis of series A (SPM).[a]
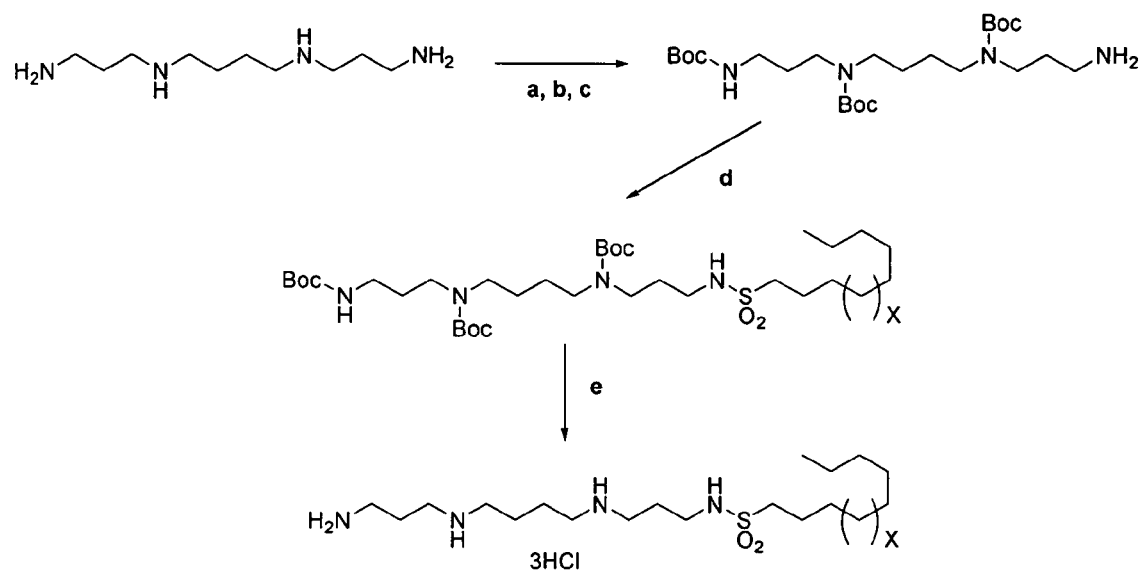
[a]Reagents and conditions: a) F$_3$CCO$_2$Et, MeOH, -78°C; b) Boc$_2$O; c) NaOH aq.; d) RSO$_2$Cl, Et$_3$N, THF; e) HCl/CH$_3$OH.

Figure 5: Synthesis of series B (HOMO-SPM).[a]
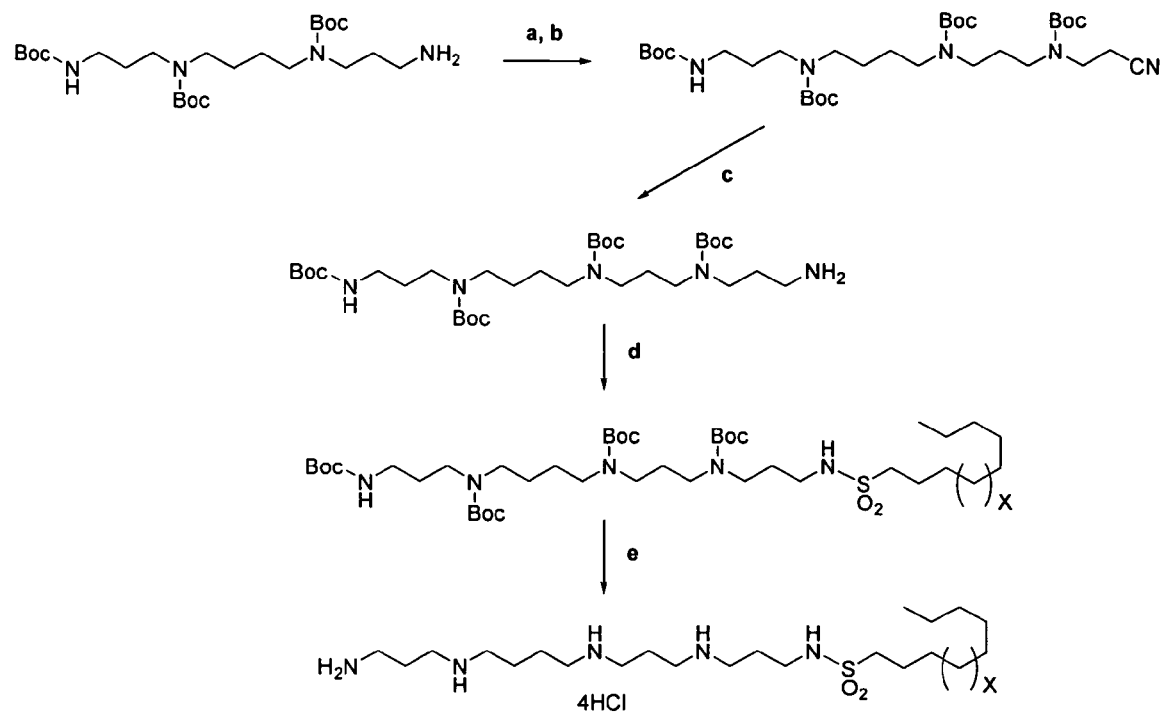
[a]Reagents and conditions: a) CH$_2$=CHCN, MeOH, 25°C; b) Boc$_2$O; c) Pd(OH)$_2$, HOAc, H$_2$; d) RSO$_2$Cl, Et$_3$N, THF; e) HCl/CH$_3$OH.

Figure 6: Synthesis of series C (BRANCHED-SPM).[a]
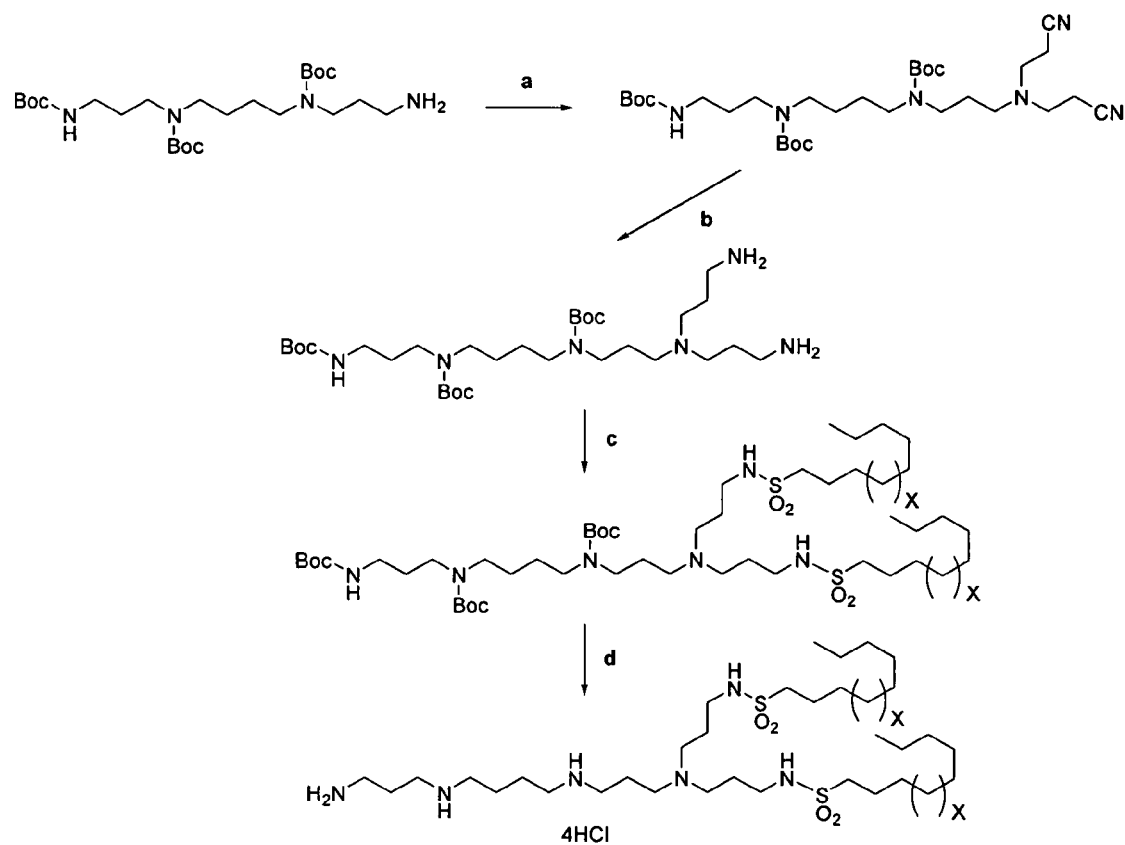
[a]Reagents and conditions: a) CH$_2$=CHCN (excess), MeOH, catalytic Dowex 50WX400 (H$^+$ form), reflux; b) Pd(OH)$_2$, HOAc, H$_2$; c) RSO$_2$Cl, Et$_3$N, THF; d) HCl/CH$_3$OH.

Figure 7: Synthesis of series D (BRANCHED-HOMO-SPM).[a]
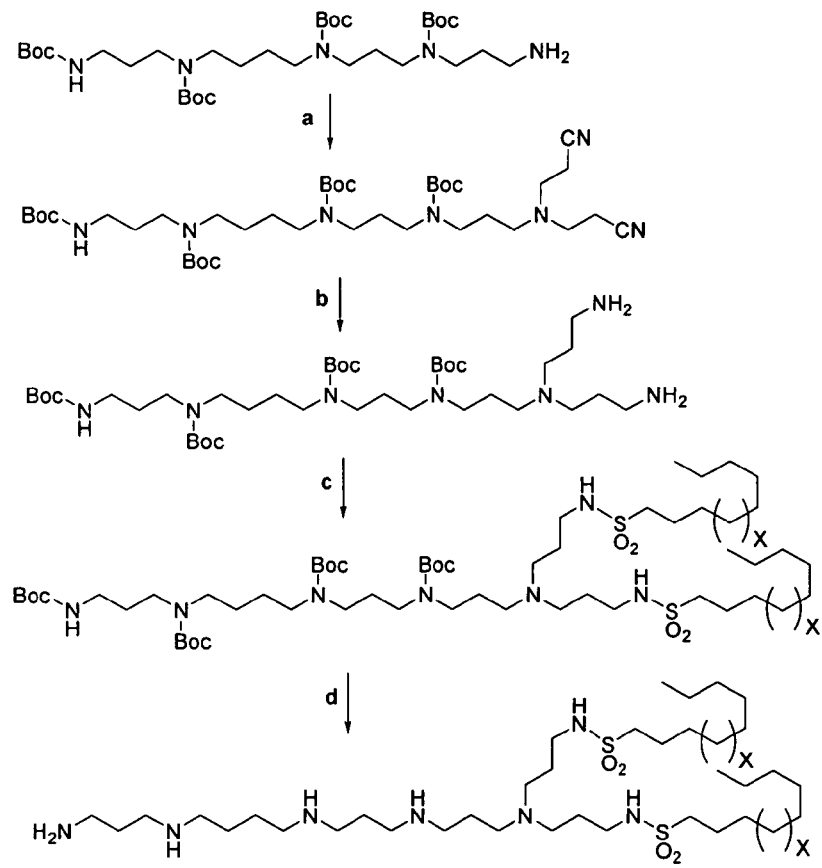
[a]Reagents and conditions: a) $CH_2=CHCN$ (excess), MeOH, catalytic Dowex 50WX400 ($H^+$ form), reflux; b) $Pd(OH)_2$, HOAc, $H_2$; c) $RSO_2Cl$, $Et_3N$, THF; d) $HCl/CH_3OH$.

Figure 8: Synthesis of series E (Bis-SUB-Bis-HOMO-SPM).[a]
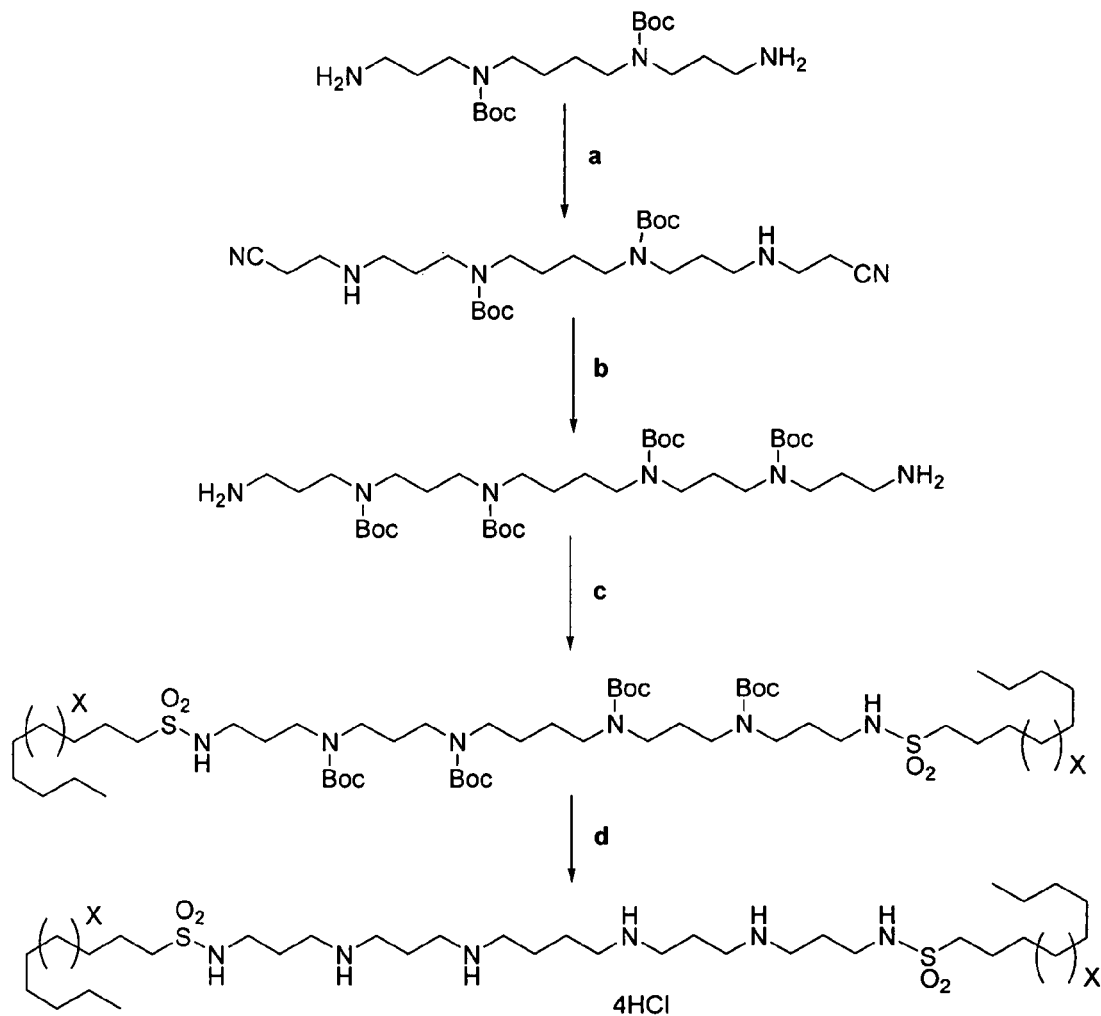
[a]Reagents and conditions: a) CH$_2$=CHCN (2 equiv), MeOH; b) i. Boc$_2$O, CH$_2$Cl$_2$; ii. Pd(OH)$_2$, HOAc, H$_2$; c) RSO$_2$Cl, Et$_3$N, THF; d) HCl/CH$_3$OH.

Figure 9: In vivo dose-response testing of polycationic sulfonamides.
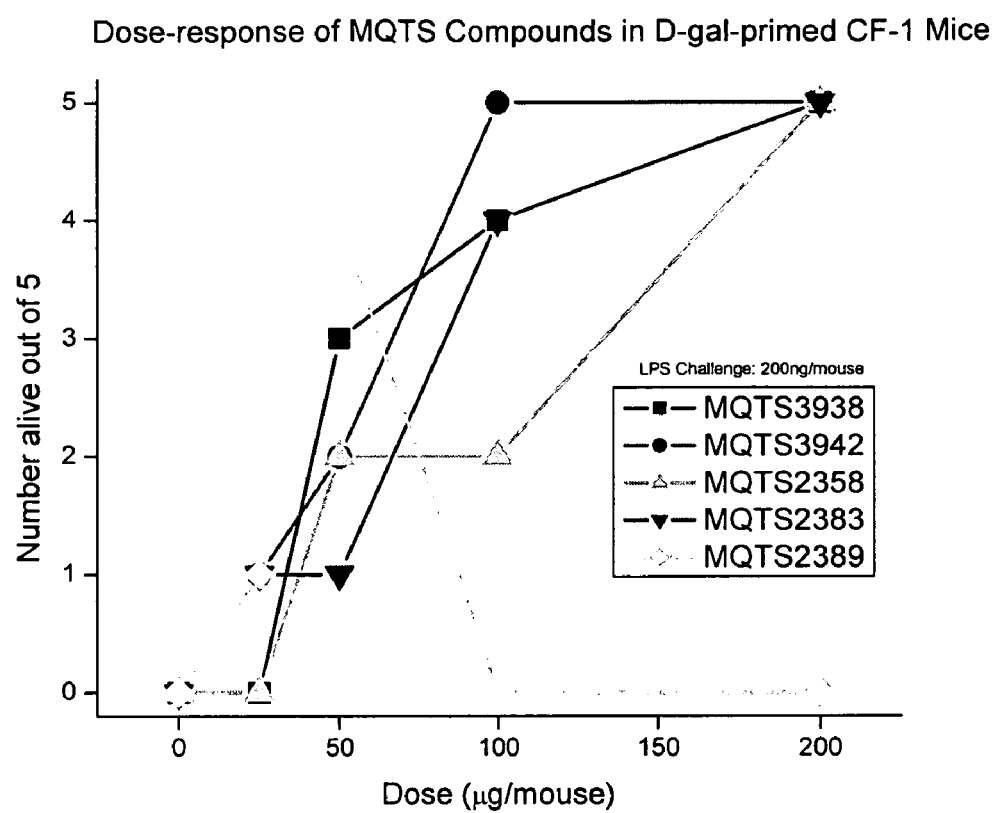

POLYCATIONIC SULFONAMIDES AND USE THEREOF

TECHNICAL FIELD

The present disclosure relates to certain lipophilic polycationic compounds. The present disclosure also relates to drug agents used to treat diseases or conditions and particularly sepsis.

Small molecule polycationic compounds bind and neutralize bacterial lipopolysaccharide endotoxins and along with test results suggest their suitability for the prevention or treatment of endotoxic shock states and/or sepsis.

BACKGROUND

Endotoxins, or lipopolysaccharides (LPS), the predominant structural component of the outer membrane of Gram-negative bacteria,[1-3] play a pivotal role in septic shock, a syndrome of systemic toxicity which occurs frequently when the body's defense mechanisms are compromised or overwhelmed, or as a consequence of antibiotic chemotherapy of serious systemic infections (Gram-negative sepsis).[4-7] Referred to as "blood poisoning" in lay terminology, Gram-negative sepsis is the thirteenth leading cause of overall mortality[8] and the number one cause of deaths in the intensive care unit,[9] accounting for more than 200,000 fatalities in the US annually.[10] Despite tremendous strides in antimicrobial chemotherapy, the incidence of sepsis has risen almost three-fold from 1979 through 2000[11] and sepsis-associated mortality has essentially remained unchanged at about 45%[12], both calling to attention the fact that aggressive antimicrobial therapy alone is insufficient in preventing mortality in patients with serious illnesses, and emphasizing an urgent, unmet need to develop therapeutic options specifically targeting the pathophysiology of sepsis.

The presence of LPS in the systemic circulation causes a widespread activation of the innate immune response[13;14] leading to the uncontrolled production of numerous inflammatory mediators, including tumor necrosis factor-α (TNF-α), interleukin-1 β (IL-1β), and interleukin-6 (IL-6), primarily by cells of the monocyte/macrophage lineage,[15;16] as well as others, such as nitric oxide produced by the endothelial cell,[17;18] which, in concert, act to cause a frequently fatal systemic inflammatory response,[19] termed 'septic shock'. The toxic moiety of LPS is its structurally conserved glycolipid component called Lipid A,[20] which is composed of a hydrophilic, bis-phosphorylated diglucosamine backbone, and a hydrophobic domain of 6 (*E. coli*) or 7 (*Salmonella*) acyl chains[20] (FIG. 1). The pharmacophore necessary for the neutralization of lipid A[21] by small molecules requires two protonatable positive charges separated by a distance of ~14 Å, enabling ionic H-bonds between the cationic groups and the lipid A phosphates; in addition, appropriately positioned pendant hydrophobic functionalities are required to further stabilize the resultant complexes via hydrophobic interactions with the polyacyl domain of lipid A (for a recent review, see Ref.[22]). These structural requisites were first identified in certain members of a novel class of compounds, the lipopolyamines, which were originally developed, and are currently being used as DNA transfection (lipofection) reagents.[23-26] In a detailed study of the effect of the hydrocarbon chain length in a homologous series of acylhomospermines, it was shown that $C_{16}$ is the ideal lipophilic substituent, corresponding to maximal affinity, optimal aqueous solubility (and bioavailability), and neutralization potency.[27]

SUMMARY

The present disclosure relates to compounds shown by the formula below representing Series A and given the general name mono-substituted spermine sulfonamide analogs (SPM), pharmaceutically acceptable salts thereof and prodrugs thereof:

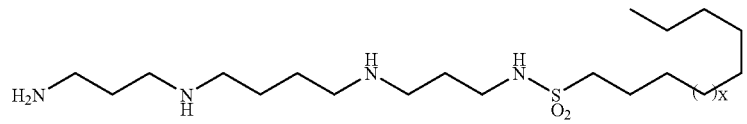

Wherein X=1 to 10.

Furthermore, the present disclosure relates to compounds shown by the formulae below representing Series B and given the general name mono-substituted homologated spermine-sulfonamide analogs (HOMO-SPM), pharmaceutically acceptable salts thereof and prodrugs thereof:

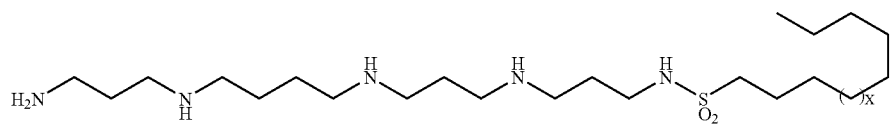

Wherein X=0 to 10.

The present disclosure also relates to compounds shown by the formula below representing Series C and given the general name bis-substituted branched spermine-sulfonamide analogs (BRANCHED-SPM), pharmaceutically acceptable salts thereof and prodrugs thereof:

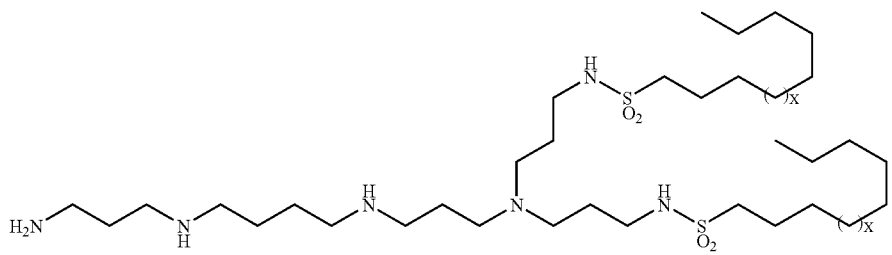

Wherein X=0 to 10

In addition, the present disclosure relates to compounds shown by the formula below representing Series D and given the general name bis-substituted branched homologated spermine-sulfonamide analogs (BRANCHED-HOMO-SPM), pharmaceutically acceptable salts thereof and prodrugs thereof:

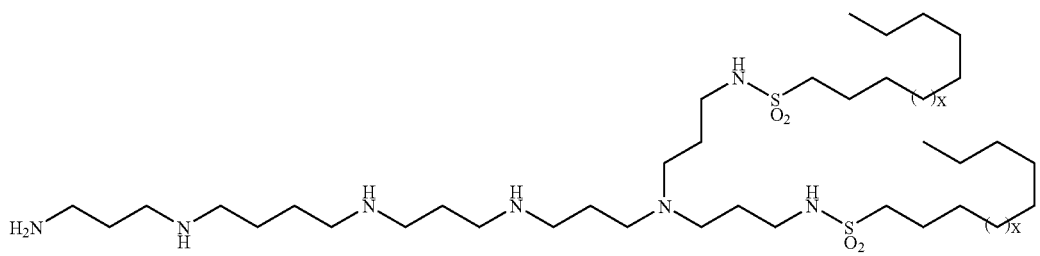

Wherein X=0 to 10

Moreover, the present disclosure relates to compounds shown by the formula below representing Series E and given the general name bis-substituted bis-homologated spermine-sulfonamide analogs (BIS-HOMO-SPM), pharmaceutically acceptable salts thereof and prodrugs thereof:

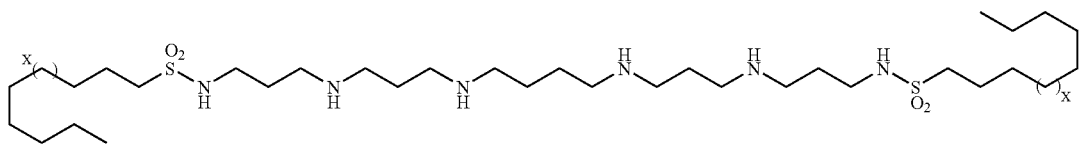

Wherein X=0 to 10

The present disclosure also relates to treating diseases involving initiation of the innate immune system by bacterial endotoxin. The exemplary disease sepsis would be treated by administering to a patient in need thereof, an effective amount of at least one compound disclosed above. A further aspect of this disclosure is concerned with treating diseases of an infectious disorder such as those caused by bacteria, fungi or viruses or other endotoxin-simulated disease states by administering to a patient in need thereof, an effective amount of at least one compound disclosed above. A still further aspect of this disclosure is concerned with treatment of diseases involving bacterial endotoxin-mediated activation of Toll-like receptors such as chronic lung disease and asthma, inflammatory eye disease and uveitis and Behcet's disease by administering to a patient in need thereof, an effective amount of at least one compound disclosed above.

Additionally, recent evidence has implicated activation of Toll-like receptors in atherosclerosis thereby establishing a link between heart disease and the defense against foreign pathogens.[28] Therefore, by inhibiting the interaction of endotoxin with its receptor, the Toll-like receptor, the disclosed compounds have usefulness for prevention of atherosclerosis.

SUMMARY OF DRAWINGS

FIG. 1 shows a schematic of the lipopolysaccharide target along with Lipid A.

FIGS. 2a and 2b illustrates the ability of representative compounds of the disclosure to bind to LPS.

FIGS. 3a and 3b illustrates the ability of representative compounds of the disclosure to inhibit the production of various cytokines.

FIG. 4 illustrates the synthetic route to produce Series A (SPM) sulfonamide analogs.

FIG. 5 illustrates the synthetic route to produce Series B (HOMO-SPM) sulfonamide analogs.

FIG. 6 illustrates the synthetic route to produce Series C (BRANCHED-SPM) sulfonamide analogs.

FIG. 7 illustrates the synthetic route to produce Series D (BRANCHED-HOMO-SPM) sulfonamide analogs.

FIG. 8 illustrates the synthetic route to produce Series E (BIS-HOMO-SPM) sulfonamide analogs.

FIG. 9 demonstrates efficacy of the described analogs in a mouse model of sepsis.

DESCRIPTION OF BEST AND VARIOUS MODES

Compounds of the present disclosure are represented by the following formula below representing Series A and given the general name mono-substituted spermine sulfonamide analogs (SPM), pharmaceutically acceptable salts thereof and prodrugs thereof:

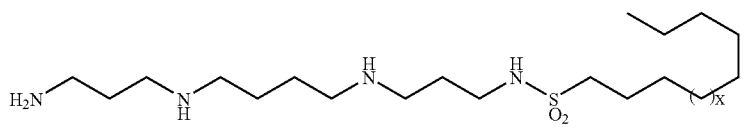

Wherein X=1 to 10.

Furthermore, the present disclosure relates to compounds shown by the formula below representing Series B and given the general name mono-substituted homologated spermine-sulfonamide analogs (HOMO-SPM, pharmaceutically acceptable salts thereof and prodrugs thereof:

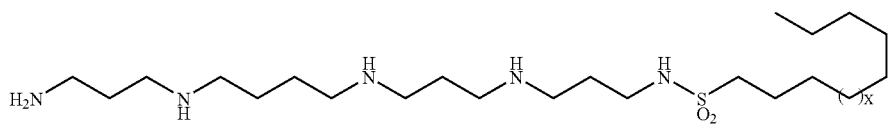

Wherein X=0 to 10.

The present disclosure also relates to compounds shown by the formula below representing Series C and given the general name bis-substituted branched spermine-sulfonamide analogs (BRANCHED-SPM), pharmaceutically acceptable salts thereof and prodrugs thereof:

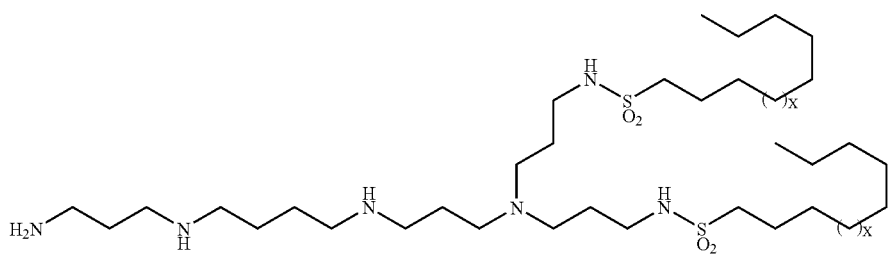

Wherein X=0 to 10

Moreover, the present disclosure relates to compounds shown by the formula below representing Series D and given the general name bis-substituted branched homologated spermine-sulfonamide analogs (BRANCHED-HOMO-SPM), pharmaceutically acceptable salts thereof and prodrugs thereof:

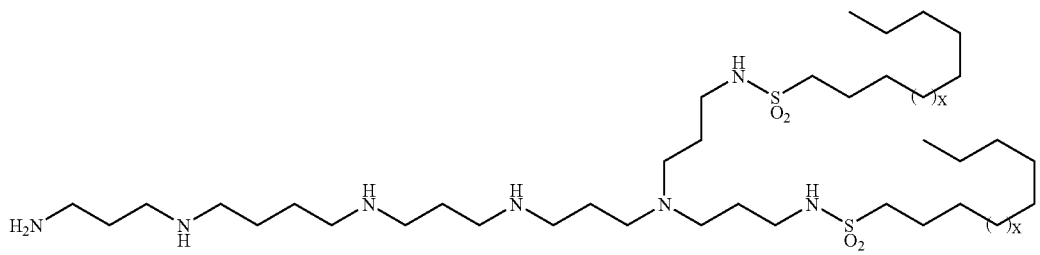

Wherein X=0 to 10

In addition, the present disclosure relates to compounds shown by the formula below representing Series E and given the general name bis-substituted bis-homologated spermine-sulfonamide analogs (BIS-HOMO-SPM), pharmaceutically acceptable salts thereof and prodrugs thereof:

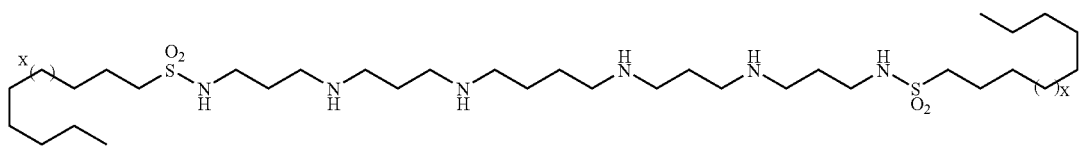

Wherein X=0 to 10

In addition to the core Lipid A portion of LPS, an additional large oligosaccharide portion exists on this biomolecule. Several potential strategies to enhance carbohydrate-binding affinity were used by targeting additional interactions with the diglucosamine backbone of lipid A. Both covalent (such as by using boronates which form esters with the vicinal cis diols)[29;30] as well as noncovalent interactions[31;32] are considered. An examination of the Protein Data Bank for lectin-sugar complexes[33;34] as well as relevant literature[35-37] point to (a) multiple H-bond donor/acceptor pairs contributing to the enthalpy of binding and (b) an unusual preponderance of aromatic side chains around the sugar binding site,[33] suggesting either multiple CH-π[38;39] or OH-π weak H-bonds.[40;41] Indeed, a lipid A receptor with a oligocyclopentane backbone substituted with amino and indole functionalities has been described.[42] A recent report described LPS-targeting peptoids isolated from a positional scanning library which incorporated various aromatic constituents along its backbone.[43] Furthermore, the crystal structure of LPS indicates a range of inter-atomic distances between 2.4-4 Å between H-bond donor/acceptor atoms on the lipid A backbone (see FIG. 1).[44] A recent report described the increased activity of homologated lipophilic spermine amides as LPS-sequestration agents (Miller, et al. (2005)). A study where a 540-membered library of polycationic bis-amides were synthesized and tested for ability to bind to LPS, inhibit cellular NO production and inhibit cytokine activation has been published.[45]

The molecules described in this invention are designed to incorporate a polycationic polyamine segment together with the optimal lipophilic segment. Each of the series of compounds described show the trend towards higher LPS-binding activity together with higher cell-based activity observed with analogs containing three or more positive charges. Furthermore, higher activity analogs can be obtained by incorporating four or more positive charges. The hydrocarbon chain that is attached via the sulfonamide group tend to lead to higher activity analogs if its length is at least fourteen carbon atoms. Optimal activity is seen with analogs with chain lengths of between fifteen and nineteen carbon atoms.

The sulfonamide group is widely used in pharmaceutical agents. Several polyamine sulfonamides have been reported in the scientific literature. Several long carbon chain containing spermine-sulfonamides have been reported by Vermeulen et al. (U.S. Pat. No. 6,172,261). Among other things, this patent discloses composition including $N^1$-(1-naphthylsulfonyl)-1,14-diamino-5,10-diazabuta-decane, $N^1$-(2-naphthylsulfonyl)-1,14-diamino-5,10-diazabuta-decane together with a variety of other heterocyclic aromatic containing spermine sulfonamides. $N^1$-Dodecanylsulfonyl-1,14-diamino-5,10-diazabuta-decane containing a twelve carbon atom sulfonamide group was disclosed in this patent. $N^1$-Dansyl-spermine and $N^1$-octanylsulfonyl-spermine were reported to be potent calmodulin and NMDA receptor antagonists.[46;47] The cytotoxic effects of several oxa-polyamine-sulfonamides has been reported.[48] A variety of aromatic sulfonamides have been effectively used as nitrogen protecting groups in polyamine synthesis.[49-53]

Synthesis of the $N^1$-sulfonylated spermine analogs described in this disclosure is accomplished most simply by the direct sulfonylation of spermine in $CH_2Cl_2$ solution. A mixture of mono- and di-together with primary and secondary amine substituted sulfonamides is obtained. An improvement to the synthetic method is enabled through the use of tri-Boc-protected spermine. The synthesis of this useful intermediate has been described by Blagbrough[54] and subsequently modified by Wellendorph.[55] Sulfonylation of triBoc-spermine followed by column chromatography then HCl-mediated deprotection is used to produce the spermine sulfonamide analogs in Series A (see Table A). This synthetic method is depicted in FIG. 4. Synthetic use of this protecting group approach for the synthesis of homologated polyamine analogs as endotoxin-sequestration agents is described by Miller et al.[56] Mono-alkylation via a Michael reaction using acrylonitrile, Boc-carbamate protection of the remaining secondary amine followed by nitrile reduction using $Pd(OH)_2$ in $CH_3CO_2H$ gives the desired homologated intermediate in pure form following column chromatography. A similar synthetic approach is used by Jasys to produce naturally occurring polyamine spider toxins.[57] As shown in FIG. 5, synthesis of the homologated spermine sulfonamides (HOMO-SPM) belonging to Series B could be accomplished by sulfonylation of the primary amine of this intermediate. Chromatography followed by acid-mediated deprotection gives the desired molecules in pure form (Table B).

Bis-alkylation of triBoc-spermine or homologated tetra-Boc-carbamate intermediates can be accomplished using an excess of acrylonitrile at elevated temperature (FIGS. 6 and 7). A literature report shows that the addition of a catalytic amount of cation exchange resin facilitates the production of the bis-adduct.[58] Application of this technique to the present problem helps to drive the conversion to the bis-adduct, which can be obtained in good yield following column chromatography. Hydrogenation using $Pd(OH)_2$ in $CH_3CO_2H$ again gives the desired product in good yield. Sulfonylation, column chromatography and HCl-mediated Boc carbamate group removal then gives the BRANCHED-SPM and BRANCHED-HOMO-SPM analogs in Table C and Table D, respectively.

The synthesis of the bis-substituted bis-homologated spermine-sulfonamide analogs (BIS-HOMO-SPM) depicted in Table E is accomplished using the $N^5,N^{10}$-di-Boc-carbamate spermine isolated from the tri-Boc-spermine synthon production (Blagbrough or Wellendorph). This synthesis is depicted in FIG. 8. Homologation on both ends of the symmetrical diamine occurs under standard conditions. Hydrogenation using $Pd(OH)_2$ in $CH_3CO_2H$ likewise occurs uneventfully. The synthesis is finished by the sulfonylation of the resulting diamine, column chromatographic purification and HCl-mediated deprotection. The various miscellaneous analogs shown in Table F are synthesized by sulfonylation of the modified polyamine under standard conditions. These analogs are purified by column chromatography over silica gel using 80:18:2 $CH_2Cl_2$/MeOH/concd $NH_4OH$. Several examples such as MQTS 2418 and MQTS 2421 are synthesized using the corresponding acid chloride instead of sulfonyl chloride. Analysis of these analogs by TLC, $^1$H-NMR, LC/MS and elemental analysis gives results consistent with their structures.

As shown by the data given in Tables A and B, the single sulfonamide-containing analogs with carbon chain lengths between C8 and C16 gives the highest activities. For example MQTS 2358, with a carbon chain length of C16, shows high affinity to LPS ($ED_{50}$ value of 3.87 µM) and potent ability to inhibit the cell-based LPS-induced cytokine production (NO $IC_{50}$ value of 0.45 µM; NFκB $IC_{50}$ value of 0.28 µM). As an additional potent example from Table B (HOMO-SPM), MQTS 2383, containing a C16 carbon chain length, shows high affinity to LPS ($ED_{50}$ value of 4.71 µM) and potent ability to inhibit the cell-based LPS-induced cytokine production (NO $IC_{50}$ value of 0.12 µM; NFκB $IC_{50}$ value of 0.20 µM).

The group of analogs containing two sulfonamide groups shown in Tables C and D demonstrate an interesting point. With these analogs, a chain length of sixteen carbon atoms is no longer the optimum length for the individual sulfonamide substituents. Alternatively, two chains of eight carbon atoms (half the size of the single sulfonamide containing analogs) give the highest activities. As shown in Table C (BRANCHED-SPM), MQTS 2406, containing two C8 carbon chains, shows high affinity to LPS ($ED_{50}$ value of 2.17 µM) and potent ability to inhibit the cell-based LPS-induced cytokine production (NFκB $IC_{50}$ value of 0.669 µM). As an additional potent example of this surprising phenomenon from Table D (BRANCHED-HOMO-SPM), MQTS 2389, again containing two C8 carbon chains, shows high affinity to LPS ($ED_{50}$ value of 2.62 µM) and potent ability to inhibit the cell-based LPS-induced cytokine production (NO $IC_{50}$ value of 0.32 µM; NFκB $IC_{50}$ value of 0.30 µM). This phenomenon is extended to the analog in Table E containing two C8 chains, MQTS 2397. This analog shows high affinity to LPS ($ED_{50}$ value of 2.6 µM) and potent ability to inhibit the cell-based LPS-induced cytokine production (NFκB $IC_{50}$ value of 0.607 µM).

These very significant findings show that inhibition of LPS-induced cell-based cytokine production by lipophilic polyamine-sulfonamides at sub-micromolar concentrations is possible. In order to further define the molecular requirements of this inhibition, a variety of analogs shown in Table F are produced. The absolute requirement for a poly-charged species is demonstrated by oxa- and carba-analogs MQTS 2370 and MQTS 2369. These non-polyamine analogs show much lower activities. Nevertheless, analogs containing the same number of charges, but in an alternative arrangement compared to spermine, still give high activities. As examples, see MQTS 2414 and MQTS 2410, which both show high affinity to LPS ($ED_{50}$ value of 4.27 µM and 3.54 µM, respectively) and potent ability to inhibit the cell-based LPS-induced cytokine production (NFκB $IC_{50}$ value of 0.363 µM and 0.379 µM, respectively). MQTS 2414 and MQT 2412 have diminished spacing between charged amine atoms while MQTS 2410 has a branched polyamine moiety. A final example of a polyamine-modified analog is given by MQTS 2416 which contains an unsaturated central core. This analog is active. The conclusion may be made that the spermine scaffold is not critically required for activity, as long as the number of charges is greater than three.

An interesting example is given by MQT 2363. This analog is specifically synthesized using $N^1,N^{14}$-Bis[trifluoroacetyl]-spermine whose internal, secondary amine groups are available for reaction. Sulfonylation, chromatography and deprotection give this analog which has a break between the three positive charges along its backbone. In comparison to the analog with three positive charged groups next to each other (MQT 2358), greatly diminished activity is observed. A similar observation of loss of biological activity by interruption of the linear charge array was made by Bergeron et al. in the design of aminopolyamines.[59]

An important conclusion may be made regarding the branched carboxamide analogs MQTS 2421 and MQTS 2418 shown in Table E. Despite having good affinity for LPS in the binding assays (1.32 µM and 1.00 µM, respectively), these analogs show greatly diminished activity in the cell-based cytokine inhibition assays in comparison to their sulfonamide counterparts ((MQTS 2406 and MQTS 2389); inhibition of NF-KB induction: 9.76 µM versus 0.669 µM for carboxamide/sulfonamide BRANCHED-SPM pair and 3.17 µM versus 0.30 µM for carboxamide/sulfonamide BRANCHED-HOMO-SPM pair). These results highlight the improved activity of the sulfonamide analogs versus their carboxamide versions. Furthermore, it emphasizes the importance of carrying out a battery of assay with which to evaluate these analogs.

Animal Testing

The in vivo activity and dose-response effect of three sulfonamide analogs using a mouse lethality assay is shown in FIG. 9. Compound MQTS 2358 represents spermine-sulfonamide Series A (SPM). Compound MQTS 2383 represents homologated spermine-sulfonamide Series B (HOMO-SPM). Compound MQTS 2389 represents branched homologated spermine-sulfonamide Series D (BRANCHED-HOMO-SPM). Also included in FIG. 9 are positive control compounds MQTS 3938 and MQTS 3942

(L-Lys(C18-alkyl)-spermine and D-Lys(C18-alkyl)-spermine, respectively) previously reported.[60] As shown in this figure, i.p. dosing with these compounds affords significant protection from super-lethal challenges with LPS in this model. Dosages of 200 μg/mouse) protected 5 out of 5 mice with all compounds except MQT 2389 which appears to have toxic effects above 50 μg/mouse dosages. Furthermore, treatment with lower dosages of these compounds also affords significant protection from the toxic effects of LPS.

Overview of Biological Activities

According to the present disclosure a terminally-placed long-chain aliphatic group is important for effective LPS neutralization. Furthermore, it is important to have this chain coupled to a polyamine containing at least three positive charges. Furthermore, it is important to the activity to have an agent which contains a sulfonamide instead of a carboxamide.

Alternative explanations for the activity of the disclosed compounds include their possible antagonism of the interaction of the MD2 co-receptor of LPS with its signaling partner TLR4. As outlined by Visintin et al., the pharmacological inhibition of the TLR4-mediated LPS-sensing system is a viable anti-immunological target.[61] The detection of Gram-negative LPS depends upon the proper function of the TLR4-MD-2 receptor complex in immune cells. E5564, an LPS antagonist, appears to inhibit cellular activation by competitively preventing the binding of LPS to MD-2.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined above.

Carboxamides, —NHC(O)R

Carbamates, —NHC(O)OR (Acyloxy)alkyl Carbamates, NHC(O)OROC(O)R

Enamines, —NHCR(=CHCO$_2$R) or —NHCR(=CH-CRONR$_2$)

Schiff Bases, —N=CR$_2$

Mannich Bases (from carboximide compounds), RCONHCH$_2$NR$_2$

Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the disclosure.

Prodrug forms of carboxyl-bearing compounds of the disclosure include esters (—CO$_2$R) where the R group corresponds to any alcohol whose release in the body through enzymatic or hydrolytic processes would be at pharmaceutically acceptable levels.

Another prodrug derived from a carboxylic acid form of the invention may be a quaternary salt type

III

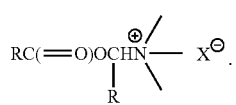

of structure described by Bodor et al., J. Med. Chem. 1980, 23, 469.

It is of course understood that the compounds of the present disclosure relate to all optical isomers and stereo-isomers at the various possible atoms of the molecule.

The compounds of this disclosure form acid and base addition salts with a wide variety of organic and inorganic acids and bases and includes the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethane-sulfonate, methanesulfonate, naphthalene-1-sulfonate, naphthalene-2-sulfonate, p-toleunesulfonate, xylene-sulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

The compounds may be utilized alone or in combination with other agents.

In another aspect of the disclosure, compositions containing the above described compounds and derivatives are provided. Typically, the compositions are formulated to be suitable for pharmaceutical or agricultural use by the inclusion of appropriate carriers or excipients.

In a further aspect of the disclosure methods for the use of the above described compounds, as well as compositions, are provided. These methods include uses of the disclosure's compounds to modulate or interrupt biological processes involving the recognition or binding of oligosaccharide-based biomolecules. Compounds of the present disclosure are useful for treating a disease or condition in which the inhibition of NO (nitric oxide) is desirable. Examples of human diseases and conditions include, but are not limited to, chronic or acute inflammation, inflammatory bowel disease (including Crohn's disease), inflammatory bowel syndrome, autoimmune diseases rheumatoid arthritis, systemic lupus erythematosus, cutaneous forms of lupus, Type 1 and Type 2 diabetes, multiple sclerosis, psoriasis, spondyloarthropathies (SpA) including spondylitis, synovitis, psoriatic arthritis and subclinical gut inflammation and infectious diseases including sepsis, spectic shock, endotoxic shock, HIV and other viral infections including cytomegalovirus, herpes simplex virus, influenza virus; infectious disorders caused by bacteria or fungi.

The present disclosure also relates to treating diseases involving initiation of the innate immune system by bacterial endotoxin. The exemplary disease sepsis would be treated by administering to a patient in need thereof, an effective amount of a compound disclosed above. A further aspect of this disclosure is concerned with treating diseases of an infectious disorder such as those caused by bacteria, fungi or viruses or other endotoxin-simulated disease states by administering to a patient in need thereof, an effective amount of a compound disclosed above. A further aspect of this disclosure is concerned with treatment of diseases involving bacterial endotoxin-mediated activation of Toll-like receptors such as chronic lung disease and asthma, inflammatory eye disease and uveitis and Behcet's disease. Additionally, recent evidence has implicated activation of Toll-like receptors in atherosclerosis thereby establishing a link between heart disease and the defense against foreign pathogens.[62] Therefore, by inhibiting the interaction of endotoxin with its receptor, the Toll-like receptor, the disclosed compounds have usefulness for prevention of atherosclerosis.

The following non-limiting examples are presented to further illustrate the present disclosure.

General experimental methods. The sources of all chemical reagents and starting materials are of the highest grade available and are used without further purification. LC/MS analyzes are performed using a Hewlett-Packard 1050 system. Detection is by a Finnigan AQA operating in ESI$^+$ mode (m/z range 140 to 1600 amu). Gradient elution from 2 to 7 min. at 0.2 mL/min. is performed using 2% to 100% $CH_3CN$ in $H_2O$ (both with 0.05% TFA) using a Waters XTerra MS $C_{18}$ 2.1×150 mm (3.5 µm) column. $^1H$ NMR spectra are recorded at 300 MHz on a Bruker AV300 spectrometer at the University of Washington, Seattle. $^1H$ NMR signals are generally multiples unless otherwise noted as s=singlet, d=doublet, t=triplet or m=multiplet. Chemical shifts are relative to external 3-(trimethylsilyl)-1-propanesulfonic acid, sodium salt.

EXAMPLE 1

Mono-substituted spermine-sulfonamide analogs (SPM)—Direct route synthetic method: Synthesis of $N^1$-Hexadecylsulfonyl-1,14-diamino-5,10-diazabuta-decane tris(hydrochloride) salt 2358—To the clear solution of 200 mg (1 mmole, 10 equiv) of spermine in 10 mL of dry $CH_2Cl_2$ is added a solution of 32 mg (0.1 mmole, 1 equiv) of hexadecylsulfonyl chloride in 1 mL of dry $CH_2Cl_2$ dropwise at 25° C. (alternatively, for di- or tri-substituted analogs shown in Table 2, 0.5 equiv of spermine is used). After stirring for 16 h the heterogeneous mixture is washed with 5% $Na_2CO_3$ and brine, dried and evaporated to give the crude product as a mixture of mono-, di- and tri-substituted spermine sulfonamides. Column chromatography is performed using 900 mg of silica gel with elution with $CH_2Cl_2$ containing 5 to 10% MeOH and 1% $NH_4OH$. Product containing fractions are combined and evaporated to give 19 as a pure oil in its free base form. This is converted to its tri-hydrochloride salt form by treatment with and evaporation from MeOH saturated with hydrogen chloride gas. $^1H$ NMR ($D_2O$, ppm): 3.07 (m, 12H), 2.08 (m, 2H), 1.88 (m, 2H), 1.74 (m, 4H), 1.26 (m, 30H), 0.82 (t, 3H). Elem. anal. calcd for $C_{26}H_{61}Cl_3N_4O_2S$: C, 52.03; H, 10.24; N, 9.33. Found: C, 51.82; H, 10.24; N, 9.37. LC/MS by ESI$^+$ mode analysis observe m/z 491 at 11.9 min retention time.

EXAMPLE 2

Mono-substituted spermine-sulfonamide analogs (TABLE A: SPM)—Alternative synthetic route method: Synthesis of $N^1$-Hexadecylsulfonyl-1,14-diamino-5,10-diazabutadecane tris(hydrochloride) salt MQTS 2358: A solution of 0.20 g (0.40 mmole) of tri-Boc-spm in 2 mL of dry $CH_2Cl_2$ is treated with 0.061 mL of triethylamine (1.10 equiv.) followed by 0.143 g of solid hexadecylsulfonyl chloride at 25° C. The resulting solution is stirred for 16 h when TLC analysis (hexane/EtOAc 2:1) shows that the reaction is complete. The reaction solution is diluted in $CH_2Cl_2$ and washed with ice-cold 0.1N HCl, $H_2O$ then brine, dried with $Mg_2SO_4$ and evaporated to give the crude product as an off-white foam. Chromatography over silica gel using hexane/EtOAc 2:1 gives 0.18 g (57% yield) of the tri-Boc intermediate. This material is completely dissolved in 5 mL of $CH_3OH$ and treated with 5 mL of 6N HCl at 25° C. After 16 h the solvents are evaporated to give 0.14 g (100%) of MQTS 2358 as its trihydrochloride salt as a white solid. Characterization exactly match that found above. Synthesis of MQTS 2351 ($C_8$), MQTS 2377 ($C_{10}$), MQTS 2357 ($C_{12}$) and MQTS 2378 ($C_{18}$) followed the same procedure except for the use of the appropriate sulfonylchloride.

$N^1$-Octanylsulfonyl-1,14-diamino-5,10-diazabutadecane tris(hydrochloride) salt MQTS 2351 ($C_8$): $^1H$ NMR ($D_2O$, ppm): 3.02 (m, 14H), 1.98 (m, 2H), 1.83 (m, 2H), 1.68 (m, 6H), 1.31 (m, 2H), 1.18 (m, 8H), 0.72 (t, 3H). Elem. anal. calcd for $C_{18}H_{45}Cl_3N_4O_2S$: C, 44.30; H, 9.29; N, 11.48. Found: C, 44.19; H, 9.25; N, 11.27. LC/MS by ESI$^+$ mode analysis observe m/z 379 at 10.7 min retention time.

$N^1$-Decanylsulfonyl-1,14-diamino-5,10-diazabutadecane tris(hydrochloride) salt MQTS 2377 ($C_{10}$): $^1H$ NMR ($D_2O$, ppm): 3.04 (m, 14H), 1.99 (m, 2H), 1.82 (m, 2H), 1.67 (m, 6H), 1.33 (m, 2H), 1.19 (m, 12H), 0.76 (t, 3H). Elem. anal. calcd for $C_{20}H_{49}Cl_3N_4O_2S$: C, 46.55; H, 9.57; N, 10.86. Found: C, 46.46; H, 9.50; N, 10.69. LC/MS by ESI$^+$ mode analysis observe m/z 407 at 10.9 min retention time.

$N^1$-Dodecanylsulfonyl-1,14-diamino-5,10-diazabutadecane tris(hydrochloride) salt MQTS 2357 ($C_{12}$): $^1H$ NMR ($D_2O$, ppm): 3.07 (m, 14H), 2.04 (m, 2H), 1.86 (m, 2H), 1.72 (m, 6H), 1.34 (m, 2H), 1.18 (m, 16H), 0.78 (t, 3H). Elem. anal. calcd for $C_{22}H_{53}Cl_3N_4O_2S$: C, 48.56; H, 9.82; N, 10.30. Found: C, 48.40; H, 9.79; N, 10.31. LC/MS by ESI$^+$ mode analysis observe m/z 435 at 11.2 min retention time.

$N^1$-Octadecanylsulfonyl-1,14-diamino-5,10-diazabutadecane tris(hydrochloride) salt MQTS 2378 ($C_{18}$): $^1H$ NMR ($D_2O$, ppm): 3.04 (m, 14H), 2.05 (m, 2H), 1.94 (m, 2H), 1.78 (m, 6H), 1.26 (m, 30H), 0.82 (t, 3H). Elem. anal. calcd for $C_{28}H_{65}Cl_3N_4O_2S$: C, 53.53; H, 10.43; N, 8.92. Found: C, 53.39; H, 10.46; N, 8.75. LC/MS by ESI$^+$ mode analysis observe m/z 519 at 12.5 min retention time.

EXAMPLE 3

Mono-substituted homologated spermine-sulfonamide analogs (TABLE B: HOMO-SPM)—Synthesis of $N^1$-Hexadecanylsulfonyl-1,18-diamino-5,9,14-triazaoctadecane tetrahydrochloride salt MQTS 2383: To the solution of 2.6 g (6.5 mmol) of triBoc-spm in 120 mL of dry $CH_3OH$ is added 0.85 mL of acrylonitrile. Following stirring for 18 h, TLC analysis ($CH_2Cl_2$/MeOH/$NH_4OH$ 90:8:2) shows that the reaction is nearly complete.

The solvent is evaporated and the oily residue is dissolved in 100 mL of $CH_2Cl_2$ and treated with 3.06 g (14 mmole, 2.15 equiv.) of $Boc_2O$. After 16 h the solvents are evaporated and the oily residue is purified by chromatography over silica gel (hexanes/EtOAc 3:2) to give 2.8 g (66%) of mono-alkylated product as a colorless oil. This intermediate is dissolved in 30 mL of glacial acetic acid and 3 g of Pd(OH)$_2$ is added. This mixture is placed under 50 psi of H$_2$ pressure and shaken for 15 h. The catalyst is removed by filtering over a pad of Celite and the pad is washed with CH$_3$OH and the combined filtrates are evaporated to give the crude product as a colorless oil. This is purified over silica gel using CHCl$_3$/MeOH/concd. NH$_4$OH, 92:8:2 to give 2.0 g (71%) colorless oil. This intermediate is also used for the synthesis of branched HOMO-spermine analogs depicted in TABLE D (see Example 5 below). A 0.20 g (0.30 mmole) portion of this material is dissolved in 7 mL of dry CH$_2$Cl$_2$ and treated with 0.063 mL (1.5 equiv) of triethylamine followed by 0.15 g (1.5 equiv.) of solid hexadecylsulfonyl chloride at 25° C. Following 16 h the reaction is diluted with CH$_2$Cl$_2$ and washed with ice-cold 0.1N HCl, H$_2$O then brine. Drying and evaporation give the crude product. Chromatography over silica gel using hexane/EtOAc 2:1 gives 0.171 g (65%) of the product as a colorless oil. This is dissolved in 5 mL CH$_3$OH and treated with 5 mL of 6N HCl at 25° C. The resulting colorless solution is stirred for 8 h when evaporation gives 0.121 g (97%) MQTS 2383 as a white solid in its tetrahydrochloride salt form. $^1$H NMR (D$_2$O, ppm): 3.05 (br s, 16H), 2.08 (br s, 4H), 1.90 (br s, 2H), 1.73 (m, 6H), 1.22 (m, 28H), 0.78 (br s, 3H). Elem. anal. calcd for C$_{29}$H$_{69}$Cl$_4$N$_5$O$_2$S: C, 50.21; H, 10.02; N, 10.09. Found: C, 50.17; H, 9.96; N, 10.11. LC/MS by ESI$^+$ mode analysis observe m/z 548 at 11.7 min retention time. Synthesis of MQTS 2379 (C$_8$), MQTS 2381 (C$_{10}$), MQTS 2382 (C$_{12}$) and MQTS 2380 (C$_{18}$) follows the same procedure except for the use of the appropriate sulfonylchloride.

N$^1$-Octanylsulfonyl-1,18-diamino-5,9,14-triazaoctadecane tetrahydrochloride salt MQTS 2379: $^1$H NMR (D$_2$O, ppm): 3.05 (m, 18H), 2.03 (m, 4H), 1.83 (m, 2H), 1.67 (m, 6H), 1.32 (m, 2H), 1.18 (m, 8H), 0.73 (t, 3H). Elem. anal. calcd for C$_{21}$H$_{53}$Cl$_4$N$_5$O$_2$S: C, 43.37; H, 9.19; N, 12.04. Found: C, 43.23; H, 9.14; N, 11.85. LC/MS by ESI$^+$ mode analysis observe m/z 426 at 10.8 min retention time.

N$^1$-Decanylsulfonyl-1,18-diamino-5,9,14-triazaoctadecane tetrahydrochloride salt MQTS 2381: $^1$H NMR (D$_2$O, ppm): 3.02 (m, 18H), 2.02 (m, 4H), 1.81 (m, 2H), 1.68 (m, 6H), 1.31 (m, 2H), 1.22 (m, 12H), 0.74 (t, 3H). Elem. anal. calcd for C$_{23}$H$_{57}$Cl$_4$N$_5$O$_2$S: C, 45.32; H, 9.42; N, 11.49. Found: C, 45.32; H, 9.45; N, 11.23. LC/MS by ESI$^+$ mode analysis observe m/z 464 at 10.9 min retention time.

N$^1$-Dodecanylsulfonyl-1,18-diamino-5,9,14-triazaoctadecane tetrahydrochloride salt MQTS 2382: $^1$H NMR (D$_2$O, ppm): 3.02 (m, 18H), 2.02 (m, 4H), 1.83 (m, 2H), 1.72 (m, 6H), 1.37 (m, 2H), 1.22 (m, 16H), 0.74 (t, 3H). Elem. anal. calcd for C$_{25}$H$_{61}$Cl$_4$N$_5$O$_2$S: C, 47.09; H, 9.64; N, 10.98. Found: C, 47.19; H, 9.68; N, 10.87. LC/MS by ESI$^+$ mode analysis observe m/z 492 at 11.1 min retention time.

N$^1$-Octadecanylsulfonyl-1,18-diamino-5,9,14-triazaoctadecane tetrahydrochloride salt MQTS 2380: $^1$H NMR (D$_2$O, ppm): 3.08 (br s, 18H), 2.12 (br s, 4H), 1.91 (br s, 2H), 1.74 (m, 6H), 1.34 (m, 2H), 1.23 (m, 28H), 0.74 (t, 3H). Elem. anal. calcd for C$_{31}$H$_{73}$Cl$_4$N$_5$O$_2$S.0.5H$_2$O: C, 50.95; H, 10.21; N, 9.58. Found: C, 51.08; H, 10.05; N, 9.32. LC/MS by ESI$^+$ mode analysis observe m/z 576 at 12.8 min retention time.

EXAMPLE 4

Bis-substituted branched spermine-sulfonamide analogs (TABLE C: BRANCHED-SPM)—Synthesis of N$^1$-Bis[N-hexadecylsulfonyl-3-aminopropyl]-1,14-diamino-5,10-diazabutadecane tetrahydrochloride salt MQTS 2396: To a solution of 2.0 g (4.0 mmol) of triBoc-spm in 100 mL of dry CH$_3$OH is added 2.7 mL (10 equiv) of acrylonitrile. A catalytic amount of Dowex 50WX400 cation-exchange resin is added (250 mg). The reaction is refluxed and after 18 h TLC analysis (CH$_2$Cl$_2$/MeOH/NH$_4$OH 90:8:2) shows that the reaction is nearly complete. The solvent is evaporated and the bis-alkylated adduct is purified by column chromatography using 1:1 hexane/EtOAc to give 2.2 g (90%) product as an oil. A 1.1 g (1.81 mmole) portion of this material is dissolved in 20 mL of glacial acetic acid and 1 g of Pd(OH)$_2$ on carbon is added. The mixture is placed under 50 psi H$_2$ pressure and shaken for 5 h. This is followed by filtration of the mixture over a Celite pad and the pad is washed twice each with CH$_3$OH and H$_2$O. The filtrate is diluted in EtOAc and 1N NaOH and the organic layer is removed, dried and evaporated to give 1.0 g (90%) clear oil as product. A 0.167 g (0.32 mmole) portion of this triamine is dissolved in 10 mL of dry CH$_2$Cl$_2$ and 0.136 mL (0.96 mmole, 3 equiv.) of triethylamine is added. To the resulting solution is added 0.171 mL (1.0 mmole, 3.1 equiv) of hexadecylsulfonyl chloride at 25° C. Following stirring for 18 h the solvents are evaporated and the residue is purified over silica gel using CHCl$_3$/CH$_3$OH/concd NH$_4$OH 98:1.8:0.2 to give 0.058 g (15%) of pure product. This material is dissolved in 5 mL of CH$_3$OH and treated with 5 mL of 6N at 25° C. for 16 h. Evaporation gives 0.038 g (75%) of MQTS 2396 as a white solid. Elem. anal. calcd for: C, 50.95; H, 10.21; N, 9.58. Found: C, 51.08; H, 10.05; N, 9.32. LC/MS by ESI$^+$ mode analysis observe m/z 894 at 18.3 min retention time. Synthesis of MQTS 2406 (C$_8$), MQTS 2419 (C$_{10}$), MQTS 2420 (C$_{12}$) and MQTS 2394 (C$_{18}$) follows the same procedure except for the use of the appropriate sulfonylchloride.

N$^1$-Bis[N-octanylsulfonyl-3-aminopropyl]-1,14-diamino-5,10-diazabutadecane tetrahydrochloride salt MQTS 2406: $^1$H NMR (D$_2$O, ppm): 3.23 (m, 6H), 3.08 (m, 18H), 2.08 (m, 4H), 1.90 (m, 4H), 1.71 (m, 8H), 1.34 (m, 4H), 1.22 (m, 16H), 0.77 (t, 6H). LC/MS by ESI$^+$ mode analysis observe m/z 669 at 11.1 min retention time.

N$^1$-Bis[N-decanylsulfonyl-3-aminopropyl]-1,14-diamino-5,10-diazabutadecane tetrahydrochloride salt MQTS 2419: $^1$H NMR (D$_2$O, ppm): 3.10 (m, 24H), 2.08 (m, 4H), 1.96 (m, 4H), 1.73 (m, 8H), 1.36 (m, 4H), 1.22 (m, 24H), 0.81 (t, 6H). LC/MS by ESI$^+$ mode analysis observe m/z 726 at 11.9 min retention time.

N$^1$-Bis[N-dodecanylsulfonyl-3-aminopropyl]-1,14-diamino-5,10-diazabutadecane tetrahydrochloride salt MQTS 2420: $^1$H NMR (D$_2$O, ppm): 3.23 (m, 6H), 3.07 (m, 18H), 2.19 (t, 4H), 2.08 (m, 4H), 1.84 (m, 4H), 1.72 (m, 4H), 1.50 (m, 4H), 1.21 (m, 16H), 0.77 (t, 6H). LC/MS by ESI$^+$ mode analysis observe m/z 669 at 11.1 min retention time.

N$^1$-Bis[N-octadecanylsulfonyl-3-aminopropyl]-1,14-diamino-5,10-diazabutadecane pentahydrochloride salt MQTS 2394: $^1$H NMR (D$_2$O, ppm): 3.23 (m, 6H), 3.08 (m, 18H), 2.08 (m, 4H), 1.90 (m, 4H), 1.71 (m, 8H), 1.34 (m, 4H), 1.22 (m, 16H), 0.77 (t, 6H). LC/MS by ESI$^+$ mode analysis observe m/z 950 at 21.5 min retention time.

EXAMPLE 5

Bis-substituted branched homologated spermine-sulfonamide analogs (TABLE D: BRANCHED-HOMO-SPM)—Synthesis of N$^1$-Bis[N-octanylsulfonyl-3-aminopropyl]-1,18-diamino-5,9,14-triazaoctadecane pentahydrochloride salt MQTS 2389: To a solution of 1.0 g (1.5 mmol) of the tetra-BocHOMO-spermine derivative produced in Example 3 above in 20 mL of dry CH$_3$OH is added 1.0 mL (10 equiv.) of acrylonitrile. A catalytic amount of Dowex 50WX400 cation-exchange resin is added (250 mg). The resulting clear mixture is heated to reflux to give a mixture of mono- and bis-addition products. The solvents are evaporated and the residue is purified by column chromatography using a 1:1 to 2:1 EtOAc/hexane solvent mixture to give 0.53 g (46%) of the bis-addition product as a colorless oil. A 0.52 g portion of this oil is dissolved in 20 mL of glacial acetic acid and treated with 0.5 g of Pd(OH)$_2$ under 50 psi H$_2$ pressure for 3.5 hrs. The resulting mixture is filtered over a pad of celite and evaporated to give 0.51 g (95%) clear oil. LC/MS analysis of this product confirms identity and purity. A 1.0 g portion of this product is dissolved in 20 mL of dry CH$_2$Cl$_2$ and treated with 0.54 mL of Et$_3$N (3 eq.) followed by 0.75 mL (3 eq.) of octanylsulfonylchloride at room temp. under an argon atmosphere. After stirring for 16 h the resulting reaction solution is evaporated and the crude residue is partitioned between 75 mL of EtOAc and 50 mL of cold 0.1N HCl. The organic layer is washed again using cold 0.1N HCl then dried and evaporated to give the crude, oily product. This is purified by silica gel chromatography using 98:2:0.2 CH$_2$Cl$_2$/MeOH/NH$_4$OH to give 0.90 g (62%) pure product. This material is dissolved in 15 mL of MeOH and treated with 15 mL of 6N HCl. The resulting solution is stirred for 16 h when the solvents are evaporated to give 0.70 g (96%) of desired product in its pentahydrochloride salt as a white solid. Elem. anal. calcd for C$_{35}$H$_{84}$Cl$_5$N$_7$O$_4$S$_2$.3/2H$_2$O: C, 44.94; H, 9.37; N, 10.48. Found: C, 44.85; H, 9.33; N, 10.43. LC/MS by ESI$^+$ mode analysis observe m/z 727 at 12.8 min retention time. Synthesis of MQTS 2417 (C$_{10}$), MQTS 2390 (C$_{12}$) and MQTS 2391 (C$_{18}$) follows the same procedure except for the use of the appropriate sulfonylchloride.

N$^1$-Bis[N-decanylsulfonyl-3-aminopropyl]-1,18-diamino-5,9,14-triazaoctadecane pentahydrochloride salt MQTS 2417: Elem. anal. calcd for C$_{39}$H$_{92}$Cl$_5$N$_7$O$_4$S$_2$.H$_2$O: C, 47.67; H, 9.64; N, 9.98. Found: C, 47.32; H, 9.59; N, 9.80. LC/MS by ESI$^+$ mode analysis observe m/z 783 at 11.6 min retention time.

N$^1$-Bis[N-dodecanylsulfonyl-3-aminopropyl]-1,18-diamino-5,9,14-triazaoctadecane pentahydrochloride salt MQTS 2390: LC/MS by ESI$^+$ mode analysis observe m/z 839 at 14.6 min retention time.

N$^1$-Bis[N-octadecanylsulfonyl-3-aminopropyl]-1,18-diamino-5,9,14-triazaoctadecane pentahydrochloride salt MQTS 2391: LC/MS by ESI$^+$ mode analysis observe m/z 951 at 20.1 min retention time.

EXAMPLE 6

Synthesis of bis-substituted bis-homologated sperminesulfonamide analogs (TABLE E: bisSUBbisHOMO-SPM)— Synthesis of N$^1$,N$^{14}$-Bis[N-octanylsulfonyl-3-aminopropyl]-1,14-diamino-5,10-diazabutadecane tetrahydrochloride salt MQTS 2397: To a solution of 2.6 g (6.5 mmole) of N$^5$,N$^{10}$-Bis[$^t$butoxycarbonyl]-1,14-diamino-5,10-diazabutadecane (N$^5$,N$^{10}$-bisBOC-spm) in 35 mL of CH$_3$OH is added 0.85 mL (2 equiv) of acrylonitrile at room temp for 16 h when TLC analysis (95:5:0.2 CH$_2$Cl$_2$/CH$_3$OH/NH$_4$OH) shows complete consumption of starting material. The solvents are evaporated and the residue is dissolved in 100 mL of CH$_2$Cl$_2$ and treated with 3 g (2.15 equiv) of Boc$_2$O. After 8 hrs the solvents are evaporated and the residue is purified by column chromatography over silica gel using 3:2 hexane/EtOAc to give 2.8 g (61%) as a clear oil. This material is dissolved in 40 mL of glacial AcOH and treated with 3 g of Pd(OH)$_2$ and 50 psi of H$_2$ pressure. After 4.5 hrs the catalyst is filtered off and the filtrated evaporated. The resulting residue is dissolved in EtOAc and washed with 1N NaOH, brine, dried and evaporated to give the crude product as an oil. This material is purified by column chromatography over silica gel using 95:5:0.5 CHCl$_3$/MeOH/NH$_4$OH to give 2.0 g (71%) clear oil. A 0.20 g (0.28 mmole) portion of this product is dissolved in 5 mL dry CH$_2$Cl$_2$ and treated with 0.12 mL (3 equiv) of triethylamine followed by 0.164 mL (3 equiv) of octanylsulfonylchloride dropwise. The reaction is stirred under argon for 16 hrs when the reaction is diluted with CH$_2$Cl$_2$, washed with 0.1N HCl and brine, dried and evaporated. The crude residue is purified over silica gel chromatography using 1:1 hex/EtOAc to give pure protected product. This is directly deprotected using 2 mL of 1:1 CH$_3$OH/6N HCl. This solution is allowed to stand for 16 hrs when evaporation gives 52 mg (23%) pure MQTS 2397 as its tetrahydrochloride salt. Elem. anal. calcd for C$_{32}$H$_{76}$Cl$_4$N$_6$O$_4$S$_2$: C, 47.16; H, 9.40; N, 10.31. Found: C, 46.99; H, 9.40; N, 10.09. LC/MS by ESI$^+$ mode analysis observe m/z 670 at 12.7 min retention time. Synthesis of MQTS 2398 (C$_{10}$), MQTS 2399 (C$_{12}$) and MQTS 2400 (C$_{18}$) and MQTI 2401 (C$_{20}$) follows the same procedure except for the use of the appropriate sulfonylchloride.

N$^1$,N$^{14}$-Bis[N-decanylsulfonyl-3-aminopropyl]-1,14-diamino-5,10-diazabutadecane tetrahydrochloride salt MQTS 2398: Elem. anal. calcd for C$_{36}$H$_{84}$Cl$_4$N$_6$O$_4$S$_2$.H$_2$O: C, 48.63; H, 9.75; N, 9.45. Found: C, 48.94; H, 9.57; N, 9.34. LC/MS by ESI$^+$ mode analysis observe m/z 726 at 13.4 min retention time.

N$^1$,N$^{14}$-Bis[N-dodecanylsulfonyl-3-aminopropyl]-1,14-diamino-5,10-diazabutadecane tetrahydrochloride salt MQTS 2399: Elem. anal. calcd for C$_{40}$H$_{92}$Cl$_4$N$_6$O$_4$S$_2$: C, 51.82; H, 10.00; N, 9.06. Found: C, 51.68; H, 9.99; N, 8.99. LC/MS by ESI$^+$ mode analysis observe m/z 782 at 15.3 min retention time.

N$^1$,N$^{14}$-Bis[N-hexadecanylsulfonyl-3-aminopropyl]-1,14-diamino-5,10-diazabutadecane tetrahydrochloride salt MQTS 2400: Elem. anal. calcd for C$_{48}$H$_{108}$Cl$_4$N$_6$O$_4$S$_2$: C, 55.47; H, 10.47; N, 8.09. Found: C, 55.28; H, 10.54; N, 7.81.

N$^1$,N$^{14}$-Bis[N-octadecanylsulfonyl-3-aminopropyl]-1,14-diamino-5,10-diazabutadecane tetrahydrochloride salt MQTS 2401:

EXAMPLE 7

Synthesis of Miscellaneous analogs (TABLE F). The various miscellaneous analogs shown in Table F are synthesized by sulfonylation of the modified polyamine under standard conditions. These analogs are purified by column chromatography over silica gel using 80:18:2 CH$_2$Cl$_2$/MeOH/concd NH$_4$OH. Several examples such as MQTS 2418 and MQTS 2421 are synthesized using the corresponding acid chloride instead of sulfonyl chloride.

MQTS 2418: LC/MS by ESI$^+$ mode analysis observe m/z 627 at 11.0 min retention time.

MQTS 2421: LC/MS by ESI$^+$ mode analysis observe m/z 570 at 11.0 min retention time.

MQTS 2363: LC/MS by ESI$^+$ mode analysis observe m/z 492 at 11.7 min retention time.

MQTS 2369: LC/MS by ESI$^+$ mode analysis observe m/z 489 at 18.9 min retention time.

MQTS 2370: LC/MS by ESI$^+$ mode analysis observe m/z 493 at 17.9 min retention time.

MQTS 2409: LC/MS by ESI$^+$ mode analysis observe m/z 477 at 11.9 min retention time.

MQTS 2410: LC/MS by ESI$^+$ mode analysis observe m/z 436 at 12.2 min retention time.

MQTS 2411: LC/MS by ESI$^+$ mode analysis observe m/z 338 at 10.8 min retention time.

MQTS 2412: LC/MS by ESI$^+$ mode analysis observed m/z 394 at 11.1 min retention time.

MQTS 2413: LC/MS by ESI$^+$ mode analysis observe m/z 365 at 10.8 min retention time.

MQTS 2414: LC/MS by ESI$^+$ mode analysis observe m/z 422 at 11.1 min retention time.

MQTS 2415: LC/MS by ESI$^+$ mode analysis observe m/z 377 at 10.8 min retention time.

MQTS 2416: LC/MS by ESI$^+$ mode analysis observe m/z 434 at 11.2 min retention time.

Rapid-throughput Fluorescence Displacement Assay for quantifying binding affinities to LPS. The relative binding affinities of the sulfonamide analogs with a recently-described high-throughput fluorescence based displacement assay, is examined using BODIPY-TR cadaverine (BC; (5-(((4-(4,4-difluoro-5-(2-thienyl)-4-bora-3a,4a-diaza-s-indacene-3-yl) phenoxy)acetyl)-amino)pentylamine, hydrochloride; obtained from Molecular probes, Inc., Eugene, Oreg.).[63;64] This assay is performed in a rapid-throughput format as follows: the first column (16 wells) of a Corning Nonbinding Surface 384-well flat-bottom black fluorescence microplate contained 15 test compounds plus polymyxin B, all at 5 mM in DMSO, and are serially diluted two-fold in 50 mM Tris buffer, pH 7.4, across the remaining 23 columns, achieving a final dilution of 0.596 nM in a volume of 40 μl. Polymyxin B (PMB), a peptide antibiotic known to bind and neutralize LPS[65] serves as the positive control and reference compound for every plate, enabling the quantitative assessment of repeatability and reproducibility (CV and Z' factors) for the assay. Automated liquid handling is performed on a Precision 2000 automated microplate pipetting system, programmed using the Precision Power software, Bio-Tek Instruments Inc., VT, USA. Results are reported as half-maximal effective displacement of probe ($ED_{50}$) (Tables A-F). In all experiments, Polymyxin B (PMB), a decapeptide antibiotic, known to bind and neutralize LPS,[66-69] is used as a reference compound.

Assessment of neutralization of LPS toxicity: NO inhibition activity. Nitric oxide production is measured as total nitrite in murine macrophage J774A.1 cells using the Griess assay[70] as described previously.[71] J774A.1 cells are plated at ~$10^5$/ml in a volume of 40 μl/well, in 384-well, flat-bottomed, cell culture treated microtiter plates and subsequently stimulated with 10 ng/ml lipopolysaccharide (LPS). Concurrent to LPS stimulation, serially diluted concentrations of test compounds are added to the cell medium and left to incubate for 16 h. Polymyxin B is used as reference compound in each plate. Positive-(LPS stimulation only) and negative-controls (J774A.1 medium only) are included in each experiment. Nitrite concentrations are measured by adding 40 μl of supernatant to equal volumes of Griess reagents (50 μl/well; 0.1% NED solution in $ddH_2O$ and 1% sulfanilamide, 5% phosphoric acid solution in $ddH_2O$) and incubating for 15 minutes at room temperature in the dark. Absorbance at 535 nm is measured using a Molecular Devices Spectramax M2 multifunction plate reader (Sunnyvale, Calif.). Nitrite concentrations are interpolated from standard curves obtained from serially diluted sodium nitrite standards. IC50 values are determined for compounds that neutralize LPS inhibit NO production in a dose-dependent manner (Tables A-F). Results in this assay parallel those in the binding assay.

Assessment of Inhibition of Cytokine Induction (NF-κB): The inhibition of induction of NF-κB (a key transcripitional activator of the innate immune system, leading to uncontrolled cytokine release[72,73] which ultimately leads to multiple organ failure and the shock syndrome) is quantified using human embryonic kidney 293 cells cotransfected with TLR4 (LPS receptor), CD14 and MD2 (co-receptors), available from InvivoGen, Inc. (HEK-Bluetm, San Diego, Calif.), as per protocols provided by the vendor. Stable expression of secreted alkaline phosphatase (seAP) under control of NF-κB/AP-1 promoters is inducible by LPS, and extracellulare seAP in the supernatant is proportional to NF-κB induction. seAP is assayed spectrophotometrically using an alkaline phosphatase-specific chromogen at 620 nm using a rapid-throughput, automated protocol employing a Bio-Tek P2000 liquid handler. Results showing the ability of polycationic sulfonamide compounds to inhibit the induction of NF-κB by LPS are shown in Tables A-F.

Mouse lethality experiments: Female, outbred, 9- to 11-week-old CF-1 mice (Charles River, Wilmington, Mass.) weighing 22-28 g are used as described elsewhere.[71] Upon arrival, the mice are allowed to acclimatize for a week prior to experimentation, housed 5 per cage in a controlled environment at the AALAC-accredited University of Kansas Animal Care Facility, and allowed access to mouse chow and water ad libitum. The animals are sensitized to the lethal effects of LPS by D-galactosamine.[74-76] The lethal dose causing 100% mortality ($LD_{100}$) dose of the batch of LPS used (*E. coli* 0111:B4 procured from Sigma) is first determined by administering D-galactosamine (800 mg/kg) and LPS (0, 10, 20, 50, 100, 200 ng/mouse) as a single injection intraperitoneally (i.p.) in freshly prepared saline to batches of five animals in a volume of 0.2 ml. The expected dose-response profile is observed in two independent experiments with all five mice receiving 100 ng succumbing within 24 h, establishing the $LD_{100}$ dose to be 100 ng/mouse. In experiments designed to test dose-response effects of the polycationic sulfonamides in affording protection against LPS-induced lethality, mice received graded doses of compound diluted in saline, i.p., in one flank, immediately before a supralethal (200 ng) LPS challenge, which is administered as a separate i.p. injection into the other flank. In experiments in which the temporal window of protection is to be examined, a fixed dose of 200 μg/mouse of compound is administered at various times, before, or after supralethal (200 ng/mouse) LPS challenge. Lethality is determined at 24 h post LPS challenge.

TABLE A

Binding affinity (BC displacement; $ED_{50}$) and biological activity (NO inhibition in murine J774 cells; $IC_{50}$; NFκβ inhibition, $IC_{50}$) of mono-substituted spermine-sulfonamide analogs (SPM).

| MQTS | X | Carbon chain-length | $ED_{50}$ value (μM) | NO inhibition $IC_{50}$ value (μM) | NFκβ inhibition $IC_{50}$ value (μM) |
|---|---|---|---|---|---|
| 2351 | 0 | C8 | 6.64 | 1.44 | 33.3 |
| 2377 | 2 | C10 | 3.7 | 4.42 | 0.50 |
| 2357 | 4 | C12 | 2.69 | 1.34 | 0.41 |

TABLE A-continued

Binding affinity (BC displacement; ED$_{50}$) and biological activity (NO inhibition in murine J774 cells; IC$_{50}$; NFκβ inhibition, IC$_{50}$) of mono-substituted spermine-sulfonamide analogs (SPM).

| MQTS | X | Carbon chain-length | ED$_{50}$ value (μM) | NO inhibition IC$_{50}$ value (μM) | NFκβ inhibition IC$_{50}$ value (μM) |
|---|---|---|---|---|---|
| 2358 | 8 | C16 | 3.87 | 0.45 | 0.28 |
| 2378 | 10 | C18 | 6.01 | 0.48 | 0.36 |

TABLE B

Binding affinity (BC displacement; ED$_{50}$) and biological activity (NO inhibition in murine J774 cells; IC$_{50}$; NFκβ inhibition, IC$_{50}$) of mono-substituted homologated spermine-sulfonamide analogs (HOMO-SPM).

| MQTS | X | Carbon chain-length | ED$_{50}$ value (μM) | NO inhibition IC$_{50}$ value (μM) | NFκβ inhibition IC$_{50}$ value (μM) |
|---|---|---|---|---|---|
| 2379 | 0 | C8 | 2.84 | 6.47 | 0.816 |
| 2381 | 2 | C10 | 2.89 | 1.09 | 0.278 |
| 2382 | 4 | C12 | 2.92 | 0.39 | 0.190 |
| 2383 | 8 | C16 | 4.71 | 0.12 | 0.200 |
| 2380 | 10 | C18 | 4.45 | 0.23 | 1.06 |

TABLE C

Binding affinity (BC displacement; ED$_{50}$) and biological activity (NO inhibition in murine J774 cells; IC$_{50}$; NFκβ inhibition, IC$_{50}$) of bis-substituted branched spermine-sulfonamide analogs (BRANCHED-SPM).

| MQTS | X | Carbon chain-length | ED$_{50}$ value (μM) | NO inhibition IC$_{50}$ value (μM) | NFκβ inhibition IC$_{50}$ value (μM) |
|---|---|---|---|---|---|
| 2406 | 0 | C8 | 2.17 | — | 0.669 |
| 2419 | 2 | C10 | 2.40 | 1.10 | 5.17 |
| 2420 | 4 | C12 | 3.98 | 2.27 | 13.2 |
| 2396 | 8 | C16 | 26.4 | 15.1 | 4.85 |
| 2394 | 10 | C18 | 28.3 | 2330 | 64 |

TABLE D

Binding affinity (BC displacement; $ED_{50}$) and biological activity (NO inhibition in murine J774 cells; $IC_{50}$; NFκβ inhibition, $IC_{50}$) of bis-substituted branched homologated spermine-sulfonamide analogs (BRANCHED-HOMO-SPM).

| MQTS | X | Carbon chain-length | $ED_{50}$ value (μM) | NO inhibition $IC_{50}$ value (μM) | NFκβ inhibition $IC_{50}$ value (μM) |
|---|---|---|---|---|---|
| 2389 | 0 | C8 | 2.62 | 0.32 | 0.30 |
| 2417 | 2 | C10 | 1.16 | 0.43 | 2.2 |
| 2390 | 4 | C12 | 6.82 | 0.51 | 16.4 |
| 2391 | 8 | C16 | 9.31 | 5.2 | 2.68 |

TABLE E

Binding affinity (BC displacement; $ED_{50}$) and biological activity (NO inhibition in murine J774 cells; $IC_{50}$; NFκβ inhibition, $IC_{50}$) of bis-substituted bis-homologated spermine-sulfonamide analogs (BIS-HOMO-SPM).

| MQTS | X | Carbon chain-length | $ED_{50}$ value (μM) | NO inhibition $IC_{50}$ value (μM) | NFκβ inhibition $IC_{50}$ value (μM) |
|---|---|---|---|---|---|
| 2397 | 0 | C8 | 2.6 | — | 0.607 |
| 2398 | 2 | C10 | 13.5 | — | 4.2 |
| 2399 | 4 | C12 | 55.2 | — | 10.3 |
| 2400 | 8 | C16 | 132.6 | — | 11.7 |
| 2401 | 10 | C18 | >5000 | — | 6.49 |

TABLE F

Binding affinity (BC displacement; $ED_{50}$) and biological activity (NO inhibition in murine J774 cells; $IC_{50}$; NFκβ inhibition, $IC_{50}$) of miscellaneous backbone-modified polyamine-sulfonamide analogs (MISC-PA).

| MQTS | Structure | $ED_{50}$ value (μM) | NO inhibition $IC_{50}$ value (μM) | NFκβ inhibition $IC_{50}$ value (μM) |
|---|---|---|---|---|
| 2370 | 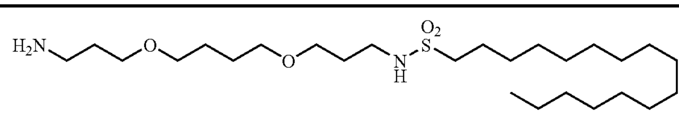 | >5000 | 30.9 | 22.4 |
| 2369 | 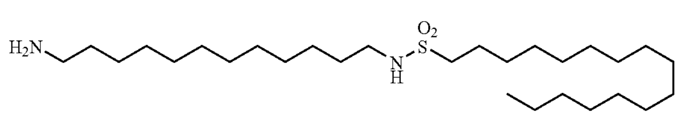 | — | — | 200 |

TABLE F-continued

Binding affinity (BC displacement; ED$_{50}$) and biological activity (NO inhibition in murine J774 cells; IC$_{50}$; NFκβ inhibition, IC$_{50}$) of miscellaneous backbone-modified polyamine-sulfonamide analogs (MISC-PA).

| MQTS | Structure | ED$_{50}$ value (μM) | NO inhibition IC$_{50}$ value (μM) | NFκβ inhibition IC$_{50}$ value (μM) |
|---|---|---|---|---|
| 2363 | 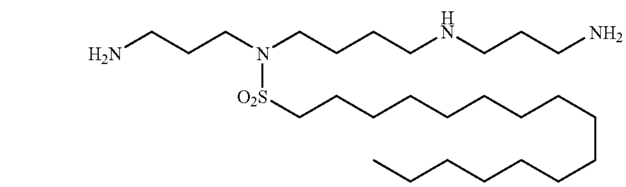 | 45.6 | 13.7 | 2.68 |
| 2413 | 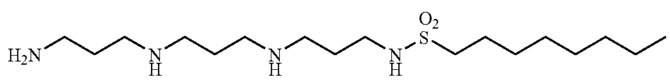 | 6.7 | — | 5.56 |
| 2414 | 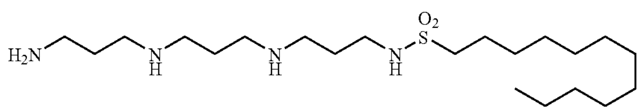 | 4.27 | — | 0.363 |
| 2410 | 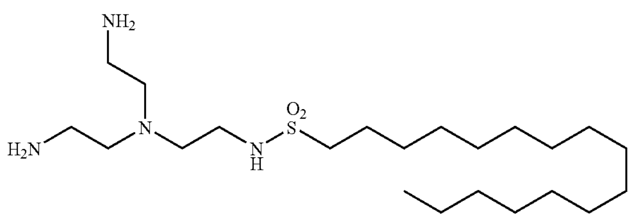 | 3.54 | — | 0.379 |
| 2409 | 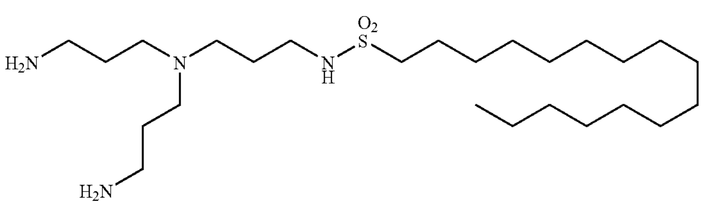 | 12.3 | — | 9.19 |
| 2416 | 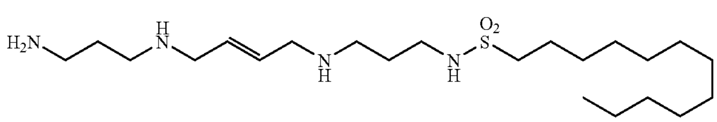 | 3.83 | — | 0.522 |
| 2411 | 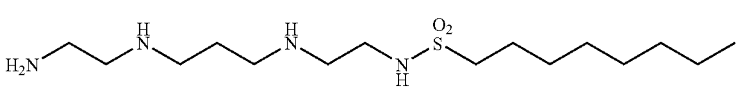 | 10.6 | — | 13.8 |
| 2412 | 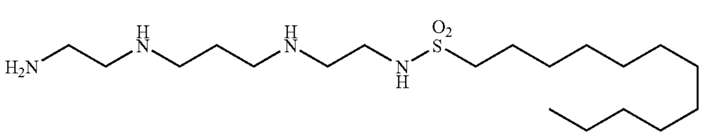 | 4.77 | — | 0.686 |
| 2415 | 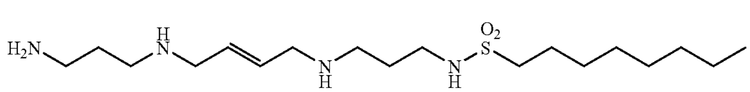 | 12.45 | — | 12.72 |

TABLE F-continued

Binding affinity (BC displacement; $ED_{50}$) and biological activity (NO inhibition in murine J774 cells; $IC_{50}$; NFκβ inhibition, $IC_{50}$) of miscellaneous backbone-modified polyamine-sulfonamide analogs (MISC-PA).

| MQTS | Structure | $ED_{50}$ value (µM) | NO inhibition $IC_{50}$ value (µM) | NFκβ inhibition $IC_{50}$ value (µM) |
|---|---|---|---|---|
| 2418 | 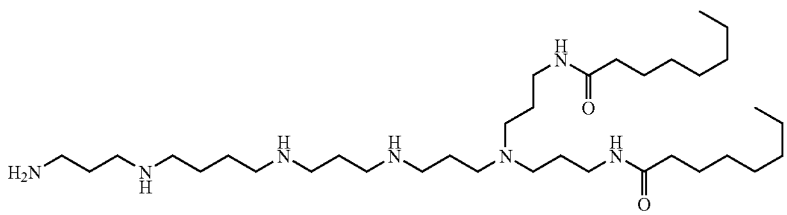 | 1 | 2.48 | 3.17 |
| 2421 | 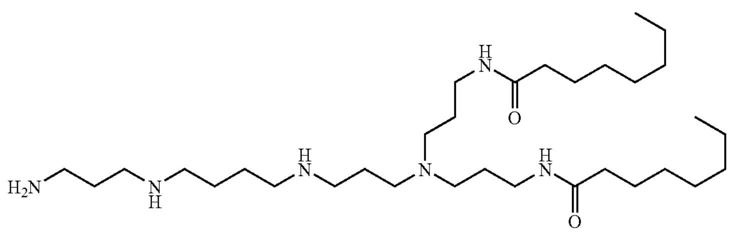 | 1.32 | 9.02 | 9.76 |

TABLE 1

Sum of carbons in lipophilic chain.

| MQTS | Structure | Σ of Carbons in Tail |
|---|---|---|
| 2351 | 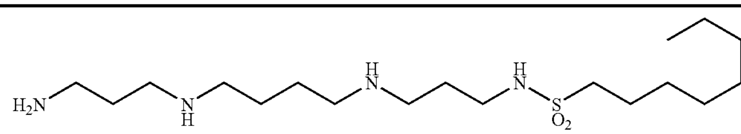 | C8 |
| 2377 | 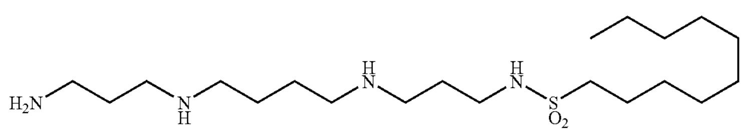 | C10 |
| 2357 | 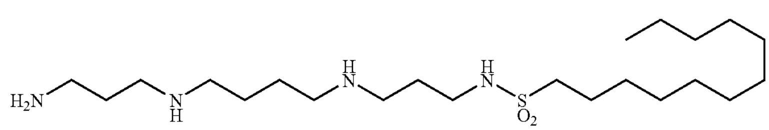 | C12 |
| 2358 | 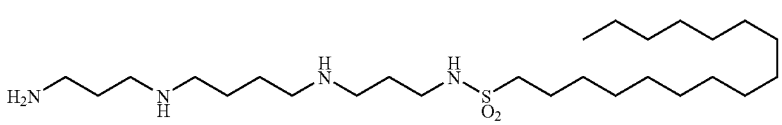 | C16 |
| 2378 | 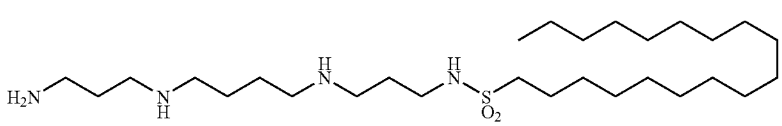 | C18 |

TABLE 1-continued
Sum of carbons in lipophilic chain.
| MQTS | Structure | Σ of Carbons in Tail |
|---|---|---|
| 2379 | 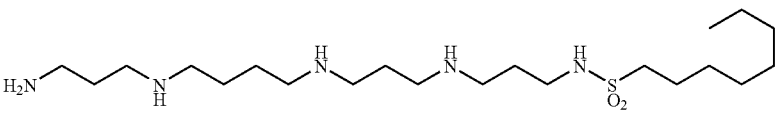 | C8 |
| 2381 | 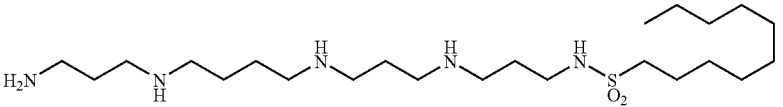 | C10 |
| 2382 | 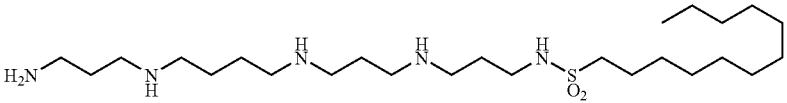 | C12 |
| 2383 | 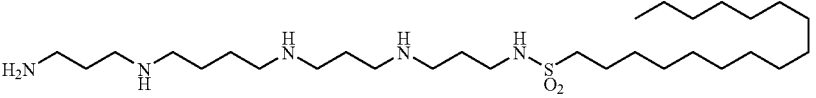 | C16 |
| 2380 | 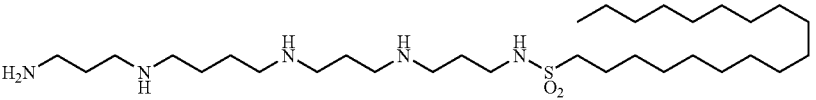 | C18 |
| 2406 | 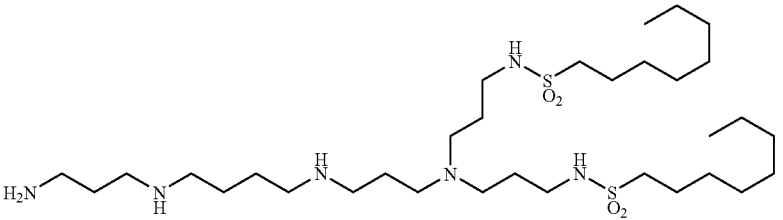 | C16 |
| 2419 | 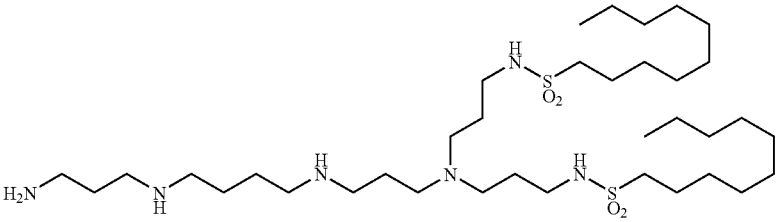 | C20 |
| 2420 | 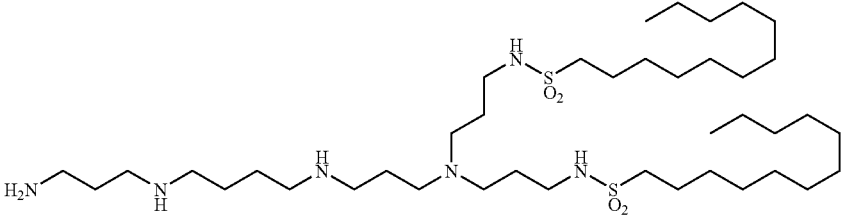 | C24 |

TABLE 1-continued
Sum of carbons in lipophilic chain.
| MQTS | Structure | Σ of Carbons in Tail |
|---|---|---|
| 2396 | 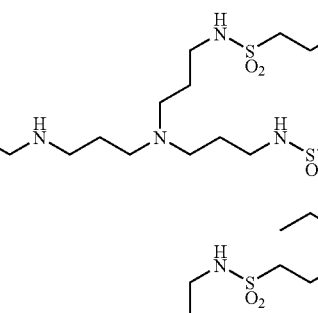 | C32 |
| 2394 | 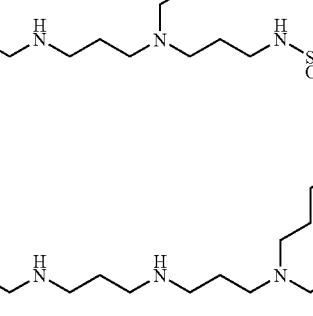 | C36 |
| 2389 | 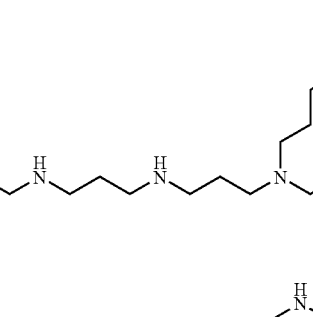 | C16 |
| 2417 | 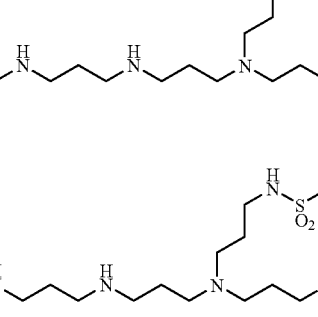 | C20 |
| 2390 | 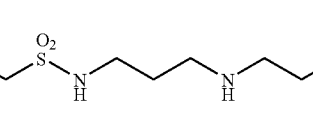 | C24 |
| 2391 | 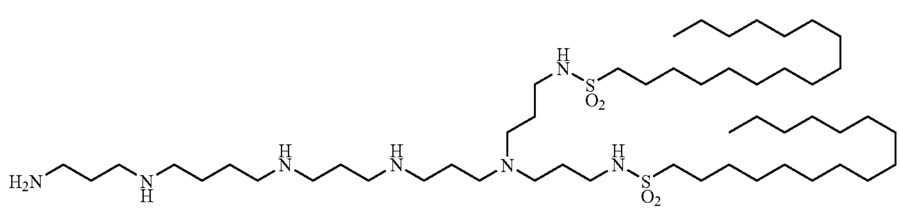 | C32 |
| 2397 | 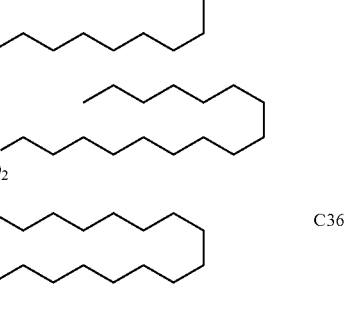 | C16 |

TABLE 1-continued

Sum of carbons in lipophilic chain.

| MQTS | Structure | Σ of Carbons in Tail |
|---|---|---|
| 2398 | 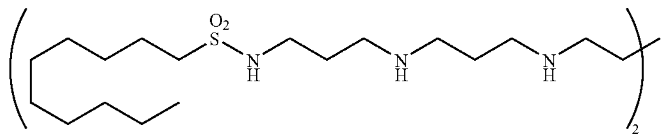 | C20 |
| 2399 | 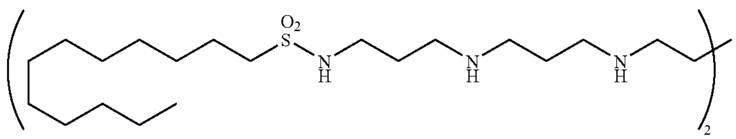 | C24 |
| 2400 | 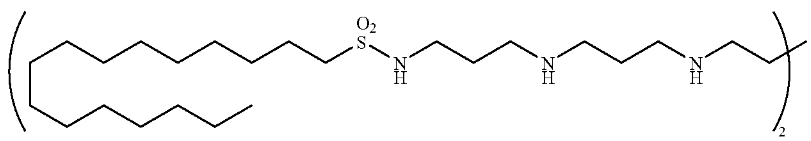 | C32 |
| 2401 | 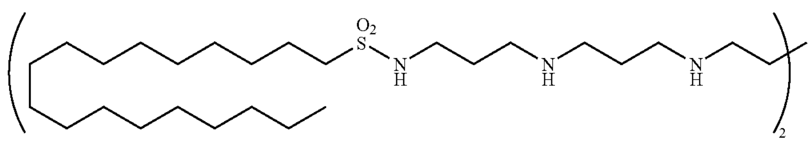 | C36 |
| 2370 | 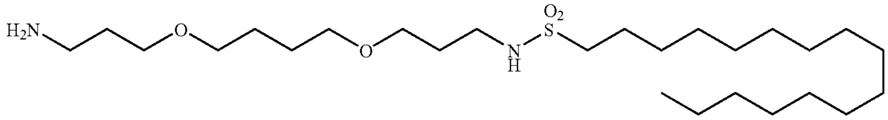 | C16 |
| 2369 | 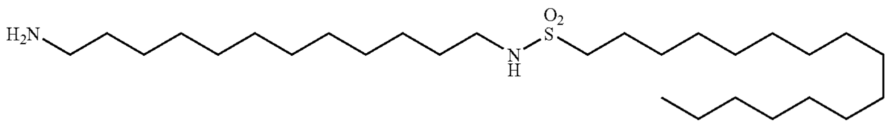 | C16 |
| 2363 | 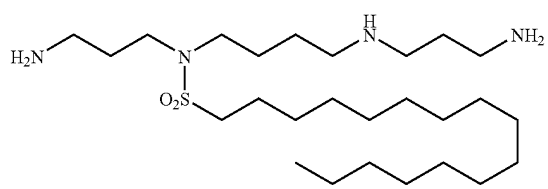 | C16 |
| 2413 | 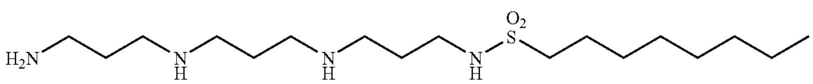 | C8 |
| 2414 | 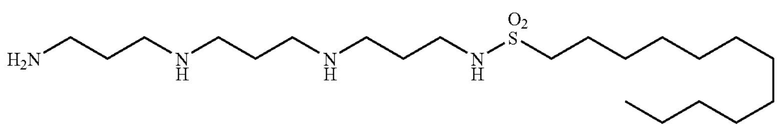 | C12 |
| 2410 | 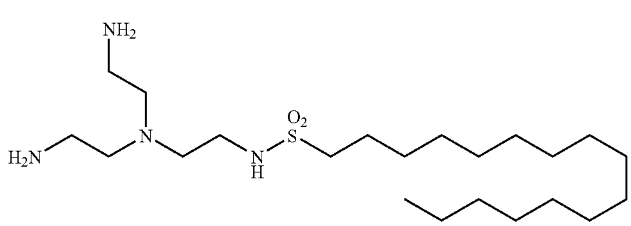 | C16 |

TABLE 1-continued

Sum of carbons in lipophilic chain.

| MQTS | Structure | Σ of Carbons in Tail |
|---|---|---|
| 2409 | 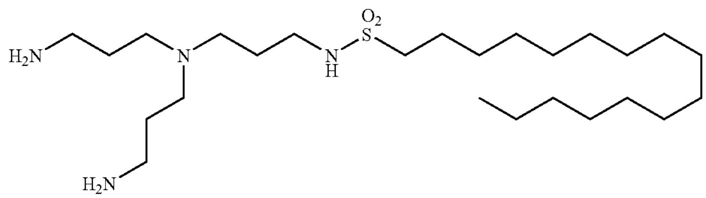 | C16 |
| 2416 | 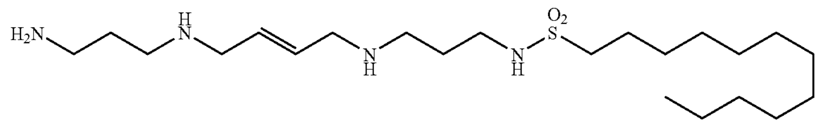 | C12 |
| 2411 | 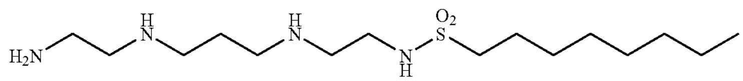 | C8 |
| 2412 | 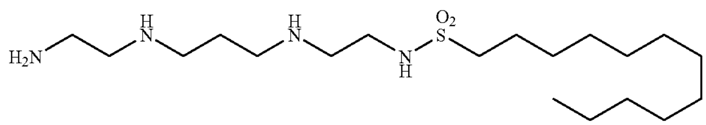 | C12 |
| 2415 | 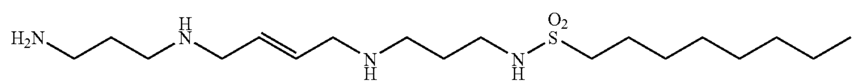 | C8 |
| 2418 | 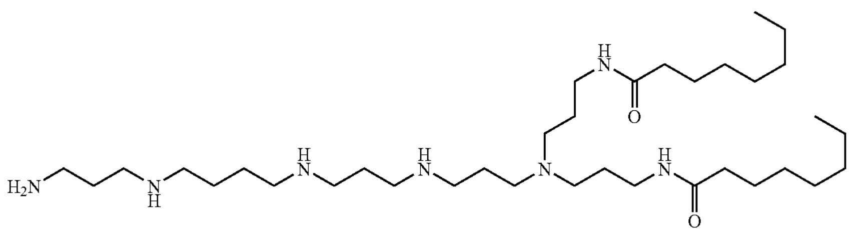 | C16 |
| 2421 | 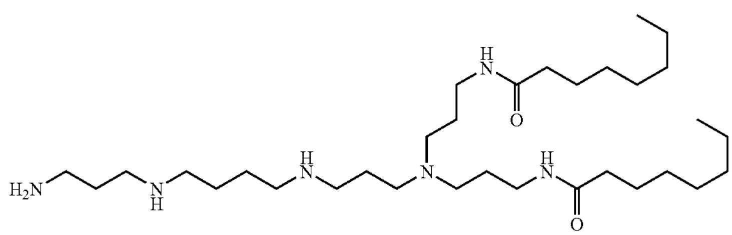 | C16 |

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment. The active ingredient can be administered employing a sustained or delayed release delivery system or an immediate release delivery system.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouth washes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present invention should be sufficient to affect a therapeutic response in the animal over a reasonable time frame. One skilled in the art will recognize that dosage will depend upon a variety of factors including a condition of the animal, the body weight of the animal, as well as the condition being treated.

A suitable dose is that which will result in a concentration of the active agent in a patient which is known to affect the desired response.

The size of the dose also will be determined by the route, timing and frequency of administration as well as the existence, nature, and extent of any adverse side effects that might accompany the administration of the compound and the desired physiological effect.

Useful pharmaceutical dosage forms for administration of the compounds according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

REFERENCE LIST

1. Lüderitz, O.; Galanos, C.; and Rietschel, E. T. Endotoxins of gram-negative bacteria. *Pharmacol. Ther.* 1982, 15, 383-402.
2. Rietschel, E. T.; Kirikae, T.; Schade, F. U.; Mamat, U.; Schmidt, G.; Loppnow, H.; Ulmer, A. J.; Zähringer, U.; Seydel, U.; Di Padova, F.; and et, a. Bacterial endotoxin: molecular relationships of structure to activity and function. *FASEB J.* 1994, 8, 217-225.
3. Rietschel, E. T.; Brade, L.; Lindner, B.; and Zähringer, U. Biochemistry of lipopolysaccharides. In *Bacterial endotoxic lipopolysaccharides, vol. I. Molecular biochemistry and cellular biology*. Morrison, D. C. and Ryan, J. L. Eds.; CRC Press: Boca Raton, 1992; pp 1-41.
4. Hurley, J. C. Antibiotic-induced release of endotoxin: A reappraisal. *Clin. Infect. Dis.* 1992, 15, 840-854.
5. Hurley, J. C. Antibiotic-induced release of endotoxin. A therapeutic paradox. *Drug Saf.* 1995, 12, 183-195.
6. Prins, J. M.; van Agtmael, M. A.; Kuijper, E. J.; van Deventer, S. J.; and Speelman, P. Antibiotic-induced endotoxin release in patients with gram-negative urosepsis: a double-blind study comparing imipenem and ceftazidime. *J. Infect. Dis.* 1995, 172, 886-891.
7. Prins, J. M.; Van Deventer, S. J. H.; Kuijper, E. J.; and Speelman, P. Clinical relevance of antibiotic-induced endotoxin release. *Antimicrob. Agents Chemother.* 1994, 38, 1211-1218.
8. Gelfand, J. A. and Shapiro, L. Cytokines and sepsis: pathophysiology and therapy. *New Horizons* 1993, 1, 13-22.
9. Gasche, Y.; Pittet, D.; and Sutter, P. Outcome and prognostic factors in bacteremic sepsis. In *Clinical trials for treatment of sepsis*. Sibbald, W. J. and Vincent, J. L. Eds.; Springer-Verlag: Berlin, 1995; pp 35-51.
10. Centers for Diseases Control. Increases in national hospital discharge survey rates for septicemia—United States, 1979-1987. *MMWR* 1990, 39, 31-34.
11. Martin, G. S.; Mannino, D. M.; Eaton, S.; and Moss, M. The epidemiology of sepsis in the United States from 1979 through 2000. *N. Engl. J. Med.* 2003, 348, 1546-1554.
12. Cross, A. and Opal, S. M. Therapeutic intervention in sepsis with antibody to endotoxin: is there a future? *J. Endotoxin Res.* 1994, 1, 57-59.
13. Ulevitch, R. J. Molecular mechanisms of innate immunity. *Immunol. Res.* 2000, 21, 49-54.
14. Ulevitch, R. J. and Tobias, P. Recognition of gram-negative bacteria and endotoxin by the innate immune system. *Curr. Opin. Immunol.* 1999, 11, 19-23.
15. Dinarello, C. A. Cytokines as mediators in the pathogenesis of septic shock. *Curr. Top. Microbiol. Immunol.* 1996, 216, 133-165.
16. Michie, H. R.; Manogue, K. R.; Spriggs, D. R.; Revhaug, A.; O'Dwyer, S.; Dinarello, C. A.; Cerami, A.; Wolff, S. M.; and Wilmore, D. W. Detection of circulating tumor necrosis factor after endotoxin administration. *N. Engl. J. Med.* 1988, 318, 1481-1486.
17. Meyer, J. and Traber, D. L. Nitric oxide and endotoxin shock. *Cardiovasc. Res.* 1992, 26, 558.
18. Wright, C. E.; Rees, D. D.; and Moncada, S. Protective and pathological roles of nitric oxide in endotoxin shock. *Cardiovasc. Res.* 1992, 26, 48-57.
19. Bone, R. C. The sepsis syndrome. Definition and general approach to management. *Clin. Chest Med.* 1996, 17, 175-181.
20. Raetz, C. R. H. and Whitfield, C. Lipopolysaccharide endotoxins. *Annu. Rev. Biochem.* 2002, 71, 635-700.
21. David, S. A.; Mathan, V. I.; and Balaram, P. Interactions of linear dicationic molecules with lipid A: Structural requisites for optimal binding affinity. *J. Endotoxin. Res.* 1995, 2, 325-336.
22. David, S. A. Towards a rational development of anti-endotoxin agents: novel approaches to sequestration of bacterial endotoxins with small molecules (Invited Review). *J. Molec. Recognition* 2001, 14, 370-387.
23. Behr, J. P.; Demeneix, B.; Loeffler, J. P.; and Perez-Mutul, J. Efficient gene transfer into mammalian primary endocrine cells with lipopolyamine-coated DNA. *Proc. Natl. Acad. Sci. USA* 1989, 86, 6982-6986.
24. Behr, J. P. Gene transfer with synthetic cationic amphiphiles: Prospects for gene therapy. *Bioconjug. Chem.* 1994, 5, 382-389.
25. Felgner, P. L.; Gadek, T. R.; Holm, M.; Roman, R.; Chan, H. W.; Wenz, M.; Northrop, J. P.; Ringold, G. M.; and Danielsen, M. Lipofection: a highly efficient, lipid-mediated DNA transfection procedure. *Proc. Natl. Acad. Sci. USA* 1987, 84, 7413-7417.

26. San, H.; Yang, Z. Y.; Pompili, V. J.; Jaffe, M. L.; Plautz, G. E.; Xu, L.; Felgner, J.; Wheeler, C. J.; Felgner, P. L.; and Gao, X. Safety and short-term toxicity of a novel cationic lipid formulation for human gene therapy. *Hum. Gene Ther.* 1993, 4, 781-788.

27. Miller, K. A.; Suresh Kumar, E. V. K.; Wood, S. J.; Cromer, J. R.; Datta, A.; and David, S. A. Lipopolysaccharide Sequestrants: Structural Correlates of Activity and Toxicity in Novel Acylhomospermines. *J. Med. Chem.* 2005, 48, 2589-2599.

28. Michelsen, K. S.; Doherty, T. M.; Shah, P. K.; and Arditi, M. Role of Toll-like receptors in atherosclerosis. *Circ. Res.* 2004, 95, e96-e97.

29. Adams, J.; Palombella, V. J.; and Elliott, P. J. Proteasome inhibition: a new strategy in cancer treatment. *Invest. New Drugs* 2000, 18, 109-121.

30. James, T. D.; Sandanayake, K. R. A. S.; and Shinkai, S. Saccharide sensing with molecular receptors based on boronic acid. *Angew. Chem. Int. Ed. Engl.* 1996, 35, 1910-1922.

31. Davis, A. P. and Wareham, R. S. Carbohydrate Recognition through Noncovalent Interactions: A Challenge for Biomimetic and Supramolecular Chemistry. *Angew. Chem. Int. Ed. Engl.* 1998, 38, 2978-2996.

32. Mazik, M.; Bandmann, H.; and Sicking, W. Molecular Recognition of Carbohydrates by Artificial Polypyridine and Polypyrimidine Receptors. *Angew. Chem. Int. Ed. Engl.* 2000, 39, 551-554.

33. Seetharaman, A.; Kanigsberg, A.; Slaaby, R.; Leffler, H.; Barondes, S. H.; and Rini, J. M. X-ray Crystal Structure of the Human Galectin-3 Carbohydrate Recognition Domain at 2.1-Å Resolution. *J. Biol. Chem.* 1998, 273, 13047-13052.

34. Tahirov, T. H.; Lu, T. H.; Liaw, Y. C.; Chen, Y.; and Lin, J. Y. Crystal Structure of Abrin-a at 2.14 Å. *J. Mol. Biol.* 1995, 250, 354-367.

35. Burke, S. D.; Zhao, Q.; Schuster, M. C.; and Kiessling, L. L. Synergistic formation of soluble lectin clusters by a templated multivalent saccharide ligand. *J. Am. Chem. Soc.* 2000, 122, 4518-4519.

36. Elgavish, S. and Shaanan, B. Lectin-carbohydrate interactions: different folds, common recognition principles. *TIBS* 1997, 22, 462-467.

37. Quicho, F. A.; Vyas, N. K.; and Spurlino, J. C. Atomic interactions between proteins and carbohydrates. *Trans. Am. Crystallogr. Assoc.* 1991, 25, 23-35.

38. Kim, E. I.; Paliwal, S.; and Wilcox, C. S. Measurements of molecular electrostatic field effects in edge-to-face aromatic interactions and CH-pi interactions with implications for protein folding and molecular recognition. *J. Am. Chem. Soc.* 1998, 120, 11192-11193.

39. Umezawa, Y. CH/pi interaction in the conformation of organic compounds. A database study. *Tetrahedron* 1999, 55, 10045-10056.

40. Allen, F. H.; Howard, J. A. K.; Hoy, V. J.; Desiraju, G. R.; Reddy, D. S.; and Wilson, C. C. First neutron diffraction analysis of an O—H/pi hydrogen bond: 2-ethynyladamantan-2-ol. *J. Am. Chem. Soc.* 1996, 118, 4081-4084.

41. Steiner, T. and Koellner, G. Hydrogen bonds with pi-acceptors in proteins: Frequencies and role in stabilizing local 3D structures. *J. Mol. Biol.* 2001, 305, 535-557.

42. Hubbard, R. D.; Horner, S. R.; and Miller, B. J. Highly Substituted ter-Cyclopentanes as Receptors for Lipid A. *J. Am. Chem. Soc.* 2001, 123, 5810-5811.

43. Mora, P.; Masip, I.; Cortes, N.; Marquina, R.; Merino, R.; Merino, J.; Carbonell, T.; Mingarro, I.; Messeguer, A.; and Perez-Paya, E. Identification from a positional scanning peptoid library of in vivo active compounds that neutralize bacterial endotoxins. *J. Med. Chem.* 2005, 48, 1265-1268.

44. Ferguson, A. D.; Hofmann, E.; Coulton, J.; Diedrichs, K.; and Welte, W. Siderophore-mediated iron transport: Crystal structure of FhuA with bound lipopolysaccharide. *Science* 1998, 2215-2220.

45. Burns, M. R.; Jenkins, S. A.; Wood, S. J.; Miller, K.; and David, S. A. Structure-activity relationships in lipopolysaccharide neutralizers: design, synthesis, and biological evaluation of a 540-membered amphipathic bisamide library. *J. Comb. Chem.* 2006, 8, 32-43.

46. Chao, J.; Seiler, N.; Renault, J.; Kashiwagi, K.; Masuko, T.; Igarashi, K.; and Williams, K. N1-dansyl-spermine and N1-(n-octanesulfonyl)-spermine, novel glutamate receptor antagonists: block and permeation of N-methyl-D-aspartate receptors. *Mol. Pharmacol.* 1997, 51, 861-871.

47. Seiler, N.; Douaud, F.; Renault, J.; Delcros, J. G.; Havouis, R.; Uriac, P.; and Moulinoux, J. P. Polyamine sulfonamides with NMDA antagonist properties are potent calmodulin antagonists and cytotoxic agents. *Int. J. Biochem. Cell Biol.* 1998, 30, 393-406.

48. Pavlov, V.; Lin, P. K.; and Rodilla, V. Biochemical effects and growth inhibition in MCF-7 cells caused by novel sulphonamido oxa-polyamine derivatives. *Cell Mol. Life Sci.* 2002, 59, 715-723.

49. McMurry, T. J.; Brechbiel, M.; Wu, C.; and Gansow, O. A. Synthesis of 2-(p-thiocyanatobenzyl)-1,4,7-triazacyclononane-1,4,7-triacetic acid: application of the 4-methoxy-2,3,6-trimethylbenzenesulfonamide protecting group in the synthesis of macrocyclic polyamines. *Bioconjug. Chem.* 1993, 4, 236-245.

50. Hidai, Y.; Kan, T.; and Fukuyama, T. Total synthesis of polyamine toxin HO-416b and Agel-489 using a 2-nitrobenzenesulfonamide strategy. *Chem. Pharm. Bull. (Tokyo)* 2000, 48, 1570-1576.

51. Bergeron, R. J.; McManis, J. S.; Liu, C. Z.; Feng, Y.; Weimar, W. R.; Luchetta, G. R.; Wu, Q.; Ortiz-Ocasio, J.; Vinson, J. R.; Kramer, D.; and. Antiproliferative properties of polyamine analogues: a structure-activity study. *J. Med. Chem.* 1994, 37, 3464-3476.

52. Saab, N. H.; West, E. E.; Bieszk, N. C.; Preuss, C. V.; Mank, A. R.; Casero, R. A., Jr.; and Woster, P. M. Synthesis and evaluation of unsymmetrically substituted polyamine analogues as modulators of human spermidine/spermine-N1-acetyltransferase (SSAT) and as potential antitumor agents. *J. Med. Chem.* 1993, 36, 2998-3004.

53. Kan, T. and Fukuyama, T. Highly versatile synthesis of nitrogen-containing compounds by means of nitrobenzenesulfonamides. *Journal of Synthetic Organic Chemistry Japan* 2001, 59, 779-789.

54. Blagbrough, I. S. and Geall, A. J. Practical synthesis of unsymmetrical polyamine amides. *Tetrahedron Letters* 1998, 39, 439-442.
55. Wellendorph, P.; Jaroszewski, J. W.; Hansen, S. H.; and Franzyk, H. A sequential high-yielding large-scale solution-method for synthesis of philanthotoxin analogues. *European Journal of Medicinal Chemistry* 2003, 38, 117-122.
56. Miller, K. A.; Suresh Kumar, E. V.; Wood, S. J.; Cromer, J. R.; Datta, A.; and David, S. A. Lipopolysaccharide sequestrants: structural correlates of activity and toxicity in novel acylhomospermines. *J. Med. Chem.* 2005, 48, 2589-2599.
57. Jasys, V. J.; Kelbaugh, P. R.; Nason, D. M.; Phillips, D.; Rosnack, K. J.; Saccomano, N. A.; Stroh, J. G.; and Volkmann, R. A. Isolation, Structure Elucidation, and Synthesis of Novel Hydroxylamine-Containing Polyamines from the Venom of the Agelenopsis-Aperta Spider. *Journal of the American Chemical Society* 1990, 112, 6696-6704.
58. Fulmer, R. W. Cyanoethylation of fatty amines using acidic ion exchange catalysis. *J. Org. Chem.* 1962, 27, 4115-4116.
59. Bergeron, R. J.; Huang, G.; McManis, J. S.; Yao, H.; and Nguyen, J. N. Synthesis and biological evaluation of aminopolyamines. *J. Med. Chem.* 2005, 48, 3099-3102.
60. Burns, M. R.; Wood, S. J.; Miller, K. A.; Nguyen, T.; Cromer, J. R.; and David, S. A. Lysine-spermine conjugates: hydrophobic polyamine amides as potent lipopolysaccharide sequestrants. *Bioorg. Med. Chem.* 2005, 13, 2523-2536.
61. Visintin, A.; Halmen, K. A.; Latz, E.; Monks, B. G.; and Golenbock, D. T. Pharmacological inhibition of endotoxin responses is achieved by targeting the TLR4 coreceptor, MD-2. *J. Immunol.* 2005, 175, 6465-6472.
62. Michelsen, K. S.; Doherty, T. M.; Shah, P. K.; and Arditi, M. Role of Toll-like receptors in atherosclerosis. *Circ. Res.* 2004, 95, e96-e97.
63. Wood, S. J.; Miller, K. A.; and David, S. A. Anti-endotoxin agents. 1. Development of a fluorescent probe displacement method for the rapid identification of lipopolysaccharide-binding agents. *Comb. Chem. High. Throughput. Screen.* 2004, 7, 239-249.
64. Wood, S. J.; Miller, K. A.; and David, S. A. Anti-endotoxin agents. 2. Pilot high-throughput screening for novel lipopolysaccharide-recognizing motifs in small molecules. *Comb. Chem. High. Throughput. Screen.* 2004, 7, 733-743.
65. Morrison, D. C. and Jacobs, D. M. Binding of polymyxin B to the lipid A portion of bacterial lipopolysaccharides. *Immunochemistry* 1976, 13, 813-818.
66. Aoki, H.; Kodama, M.; Tani, T.; and Hanasawa, K. Treatment of sepsis by extracorporeal elimination of endotoxin using polymyxin B-immobilized fiber. *Am. J. Surg.* 1994, 167, 412-417.
67. Bucklin, S. E.; Lake, P.; Logdberg, L.; and Morrison, D. C. Therapeutic efficacy of a polymyxin B-dextran 70 conjugate in experimental model of endotoxemia. *Antimicrob. Agents Chemother.* 1995, 39, 1462-1466.
68. Mayumi, T.; Takezawa, J.; Takahashi, H.; Kuwayama, N.; Fukuoka, T.; Shimizu, K.; Yamada, K.; Kondo, S.; and Aono, K. Low-dose intramuscular polymyxin B improves survival of septic rats. *Shock* 1999, 11, 82-86.
69. Stokes, D. C.; Shenep, J. L.; Fishman, M. L.; Hidner, W. K.; Bysani, G. K.; and Rufus, K. Polymyxin B prevents lipopolysaccharide-induced release of tumor necrosis factor—from alveolar macrophages. *J. Infect. Dis.* 1989, 160, 52-57.
70. Green, L. C.; Wagner, D. A.; Glogowski, J.; Skipper, P. L.; Wishnok, J. S.; and Tannenbaum, S. R. Analysis of nitrate, nitrite and [15-N] nitrate in biological fluids. *Anal. Biochem.* 1982, 126, 131.
71. David, S. A.; Silverstein, R.; Amura, C. R.; Kielian, T.; and Morrison, D. C. Lipopolyamines: novel antiendotoxin compounds that reduce mortality in experimental sepsis caused by gram-negative bacteria. *Antimicrob. Agents Chemother.* 1999, 43, 912-919.
72. Ishikawa, Y.; Mukaida, N.; Kuno, K.; Rice, N.; Okamoto, S.; and Matsushima, K. Establishment of lipopolysaccharide-dependent nuclear factor kappa B activation in a cell-free system. *J. Biol. Chem.* 1995, 270, 4158-4164.
73. Shakhov, A. N.; Collart, M. A.; Vassalli, P.; Nedospasov, S. A.; and Jongeneel, C. V. Kappa B-type enhancers are involved in lipopolysaccharide-mediated transcriptional activation of the tumor necrosis factor alpha gene in primary macrophages. *J. Exp. Med.* 1990, 171, 35-47.
74. Cook, E. B.; Stahl, J. L.; Lowe, L.; Chen, R.; Morgan, E.; Wilson, J.; Varro, R.; Chan, A.; Graziano, F. M.; and Barney, N. P. Simultaneous measurement of six cytokines in a single sample of human tears using microparticle-based flow cytometry: allergics vs. non-allergics. *J. Immunol. Methods* 2001, 254, 109-116.
75. Freudenberg, M. A. and Galanos, C. Tumor necrosis factor alpha mediates lethal activity of killed Gram-negative abd Gram-positive bacteria in D-galactosamine-treated mice. *Infect. Immun.* 1991, 59, 2110-2115.
76. Tracey, K. J. and Cerami, A. Tumor necrosis factor, other cytokines and disease. *Annu. Rev. Cell Biol.* 1993, 9, 317-343.

What is claimed is:
1. A compound selected from the group consisting of Series A represented by the formula, wherein X=8 to 10:

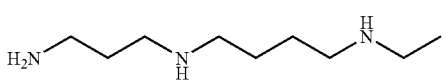

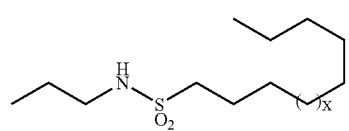

Series B represented by the formula, wherein X=0 to 10:

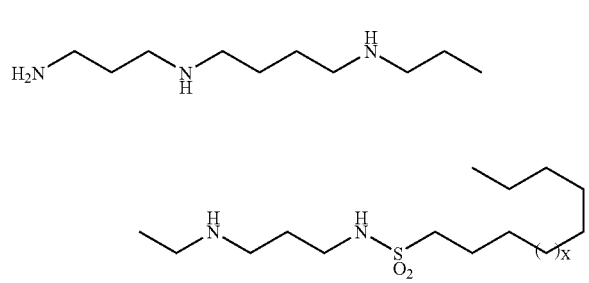

Series C represented by the formula, wherein X=0 to 10:

Series D represented by the formula, wherein X=0 to 10:

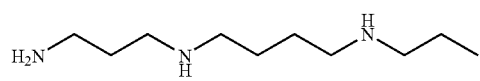

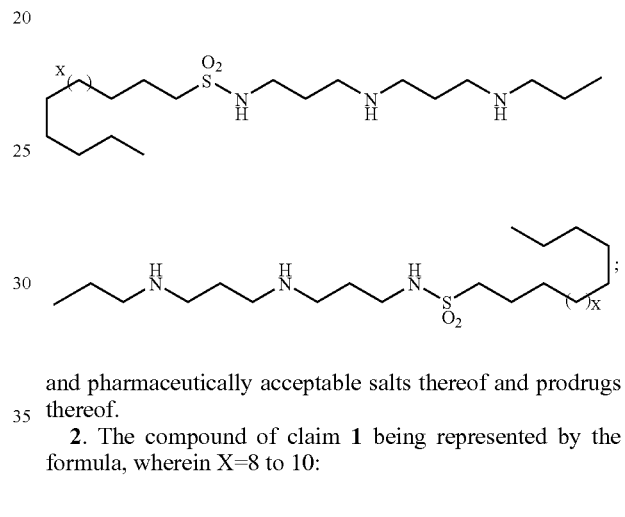

and Series E represented by the formula, wherein X=0 to 10:

and pharmaceutically acceptable salts thereof and prodrugs thereof.

2. The compound of claim 1 being represented by the formula, wherein X=8 to 10:

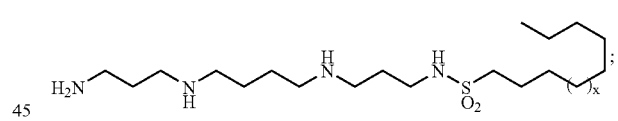

and pharmaceutically acceptable salts thereof and prodrugs thereof.

3. The compound of claim 1 being represented by the formula, wherein X=0 to 10:

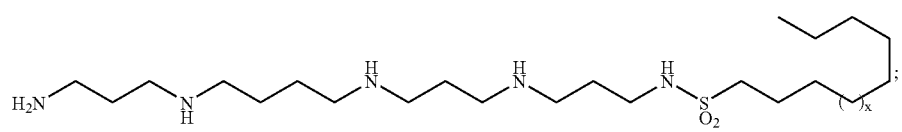

and pharmaceutically acceptable salts thereof and prodrugs thereof.

4. The compound of claim 1 being represented by the formula, wherein X=0 to 10:

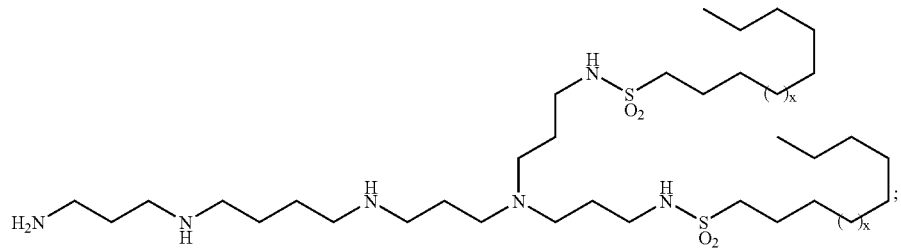

and pharmaceutically acceptable salts thereof and prodrugs thereof.

5. The compound of claim 1 being represented by the formula, wherein X=0 to 10:

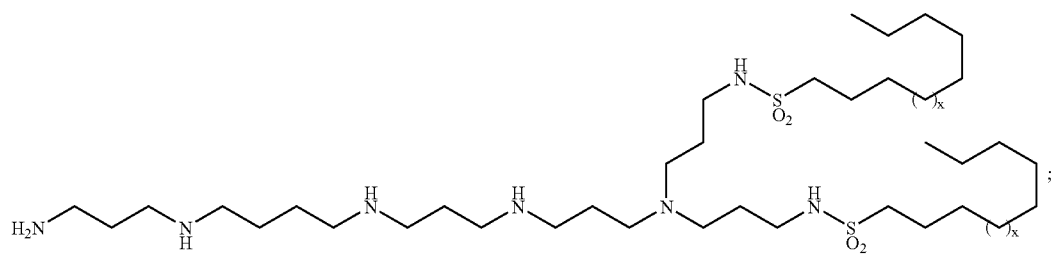

and pharmaceutically acceptable salts thereof and prodrugs thereof.

6. The compound of claim 1 being represented by the formulae, wherein X=0 to 10:

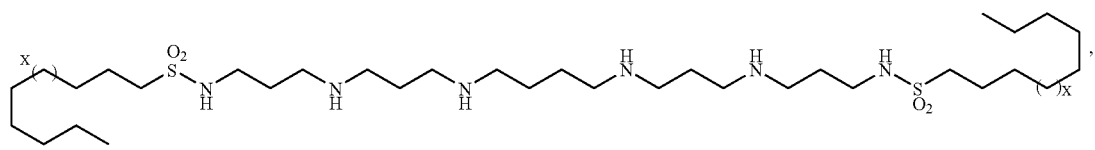

and pharmaceutically acceptable salts thereof and prodrugs thereof.

7. A method to modulate or interrupt inflammatory biological processes which involve prevention of the binding of endotoxins with their biological receptors by administering an effective amount of a compound selected from the group consisting of Series A represented by the formula, wherein X=1 to 10, (except where X=4):

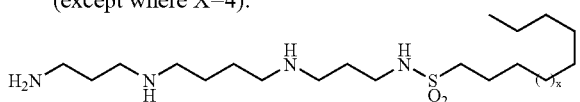

Series B represented by the formula, wherein X=0 to 10:

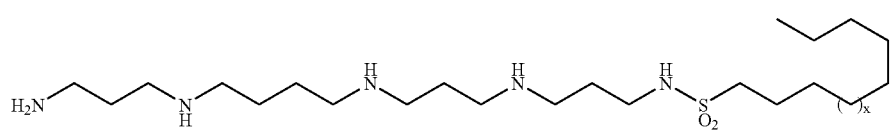

Series C represented by the formula, wherein X=0 to 10:

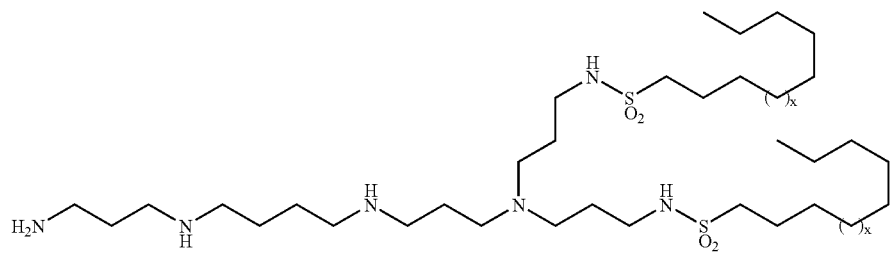

Series D represented by the formula, wherein X=0 to 10:

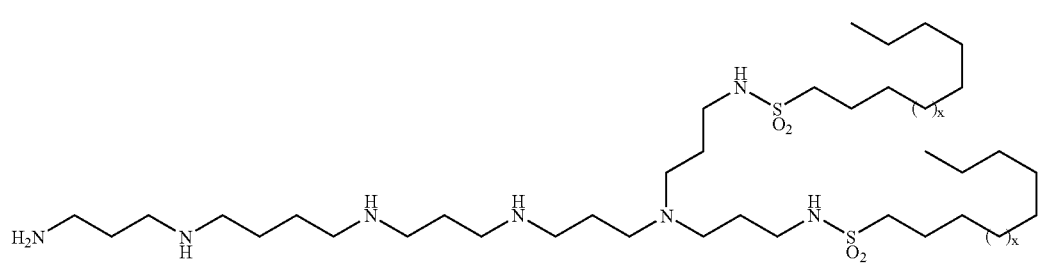

and Series E represented by the formula, wherein X=0 to 10:

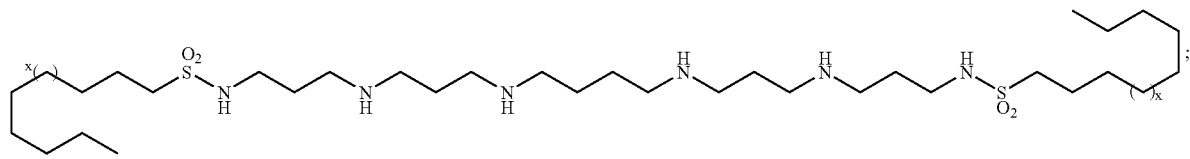

and pharmaceutically acceptable salts thereof and prodrugs thereof.

8. The method according to claim 7 which comprises treating sepsis or sepsis-like conditions in mammals.

9. The method according to claim 7 which comprises treating disease states associated with endotoxin-mediated activation of an immune response.

10. A pharmaceutical composition comprising a compound according to any one of claims 1 to 6 and a pharmaceutically acceptable carrier.

11. A method for treating a disease or condition in which the inhibition of nitric oxide production is desirable which comprising administering to a patient in need thereof an effective amount of a compound selected from the group consisting of Series A represented by the formula, wherein X=1 to 10, (except where X=4):

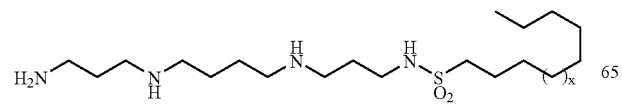

Series B represented by the formula, wherein X=0 to 10:

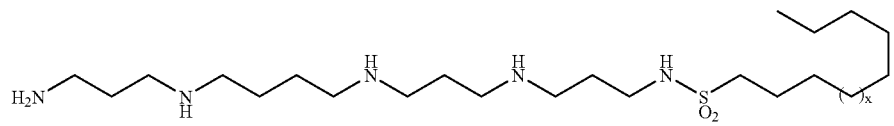

Series C represented by the formula, wherein X=0 to 10:

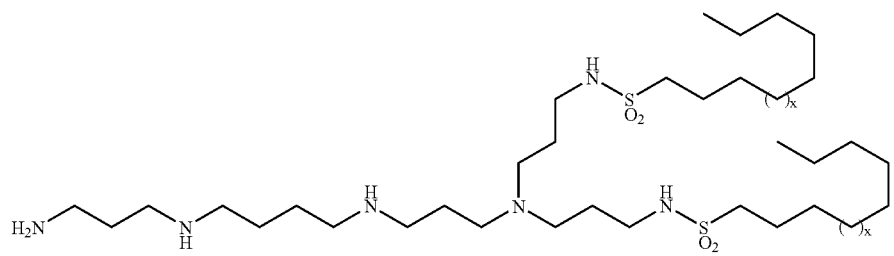

Series D represented by the formula, wherein X=0 to 10:

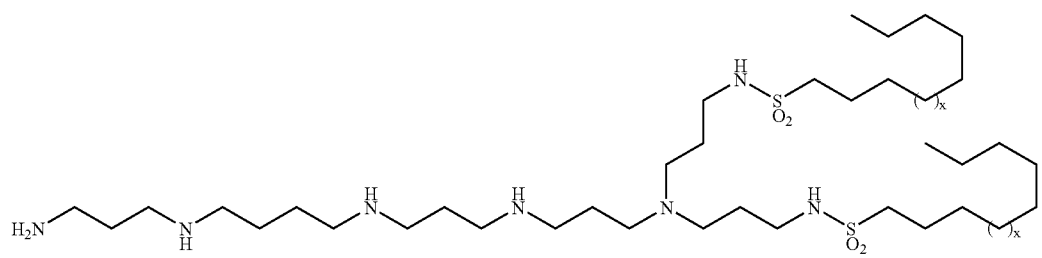

and Series E represented by the formula, wherein X=0 to 10:

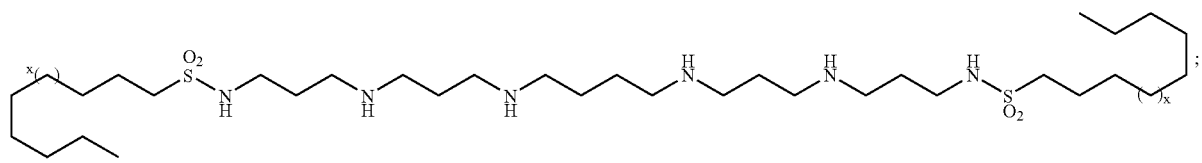

and pharmaceutically acceptable salts thereof and prodrugs thereof.

12. A method for treating a patient suffering from a disease involving a endotoxin-mediated activation of Toll-like receptors, inflammatory eye disease and uveitis, Behcet's disease or atherosclerosis which comprises administering to said patient an effective amount of a compound selected from the group consisting of Series A represented by the formula, wherein X=1 to 10, (except where X=4):

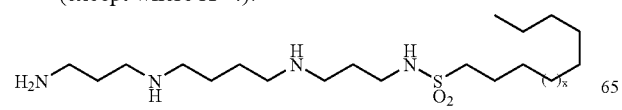

Series B represented by the formula, wherein X=0 to 10:

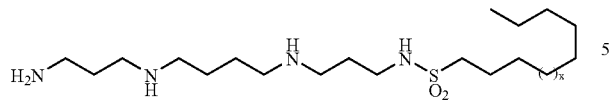

Series C represented by the formula, wherein X=0 to 10:

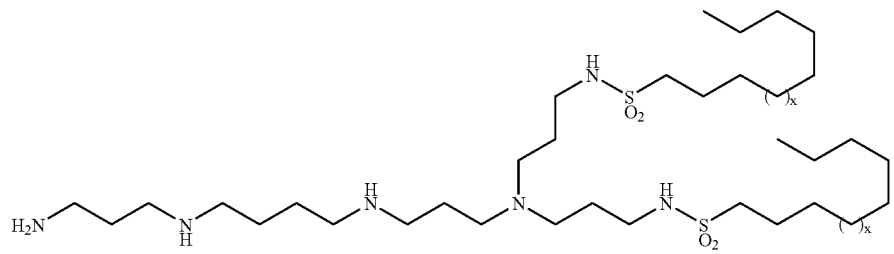

Series D represented by the formula, wherein X=0 to 10:

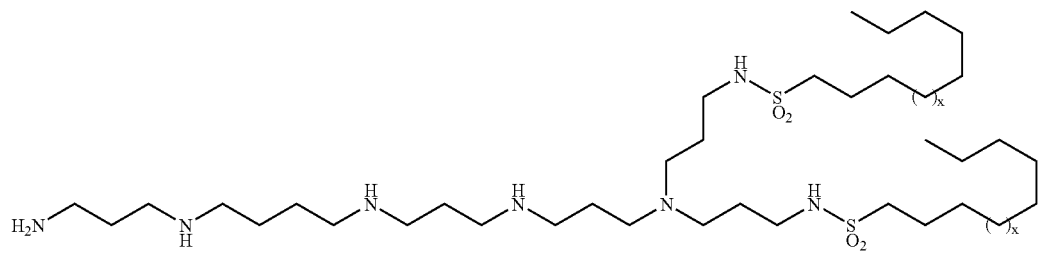

and Series E represented by the formula, wherein X=0 to 10:

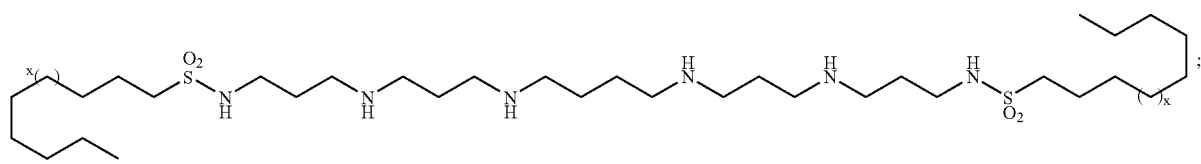

and pharmaceutically acceptable salts thereof and prodrugs thereof.

13. The method according to claim 12 wherein said endotoxin-mediated activation of Toll-like receptors is selected from the group consisting of chronic lung disease and asthma.

14. A method for treating a patient suffering from sepsis which comprises administering to said patient an effective amount of a compound of claim 2 represented by the formula, wherein X=8 to 10:

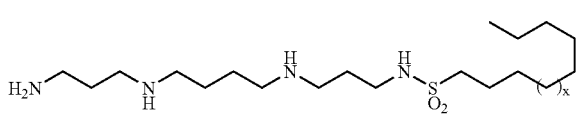

and pharmaceutically acceptable salts thereof.

15. A method for treating a patient suffering from sepsis which comprises administering to said patient an effective amount of a compound of claim 1 being represented by the formula, wherein X=0 to 10:

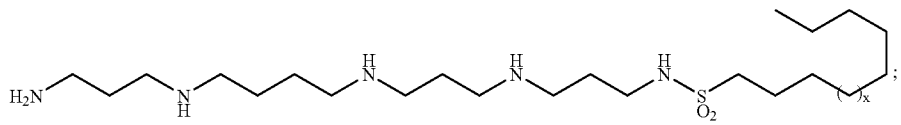

and pharmaceutically acceptable salts.

16. A method for treating a patient suffering from sepsis which comprises administering to said patient an effective amount of a compound of claim 1 represented by the formula, wherein X=0 to 10:

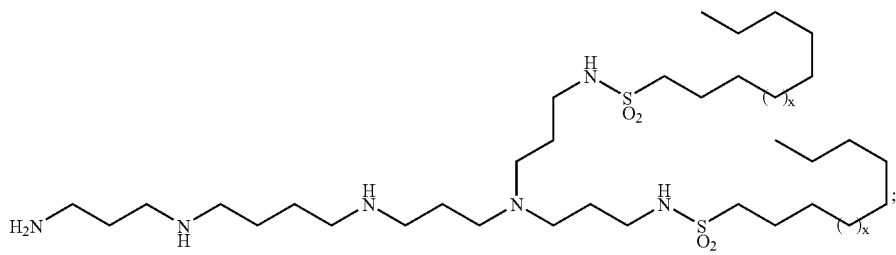

and pharmaceutically acceptable salts thereof.

17. A method for treating a patient suffering from sepsis which comprises administering to said patient an effective amount of a compound of claim 1 being represented by the formula, wherein X=0 to 10:

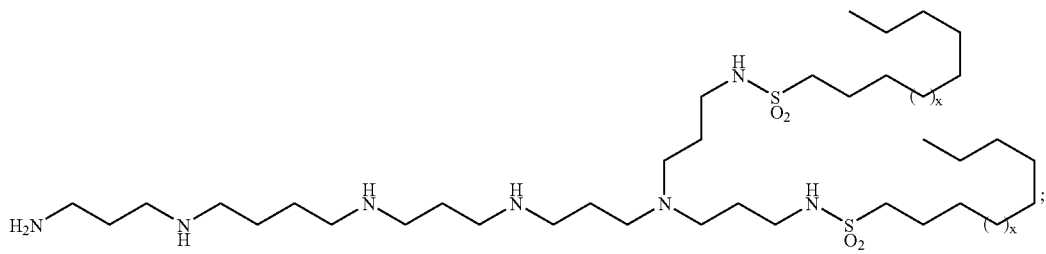

and pharmaceutically acceptable salts thereof.

18. A method for treating a patient suffering from sepsis which comprises administering to said patient an effective amount of a compound of claim 1 being represented by the formulae, wherein X=0 to 10:

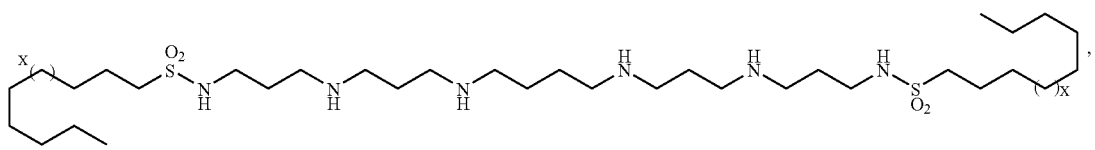

and pharmaceutically acceptable salts thereof.

* * * * *